(12) United States Patent
Shewale et al.

(10) Patent No.: US 11,406,577 B2
(45) Date of Patent: Aug. 9, 2022

(54) ALIPHATIC ANIONIC COMPOUNDS AND OXIDATIVE COMPOUNDS WITH IMPROVED STABILITY AND EFFICACY FOR USE IN PHARMACEUTICAL COMPOSITIONS

(71) Applicant: Micropure, Inc., Scottsdale, AZ (US)

(72) Inventors: Jaiprakash G. Shewale, Cave Creek, AZ (US); William E. Cooley, Wyoming, OH (US); James L. Ratcliff, Scottsdale, AZ (US); Esmeralda Ann Garcia-Smith, Centerton, AR (US)

(73) Assignee: Micropure, Inc., Scottsdale, AZ (US)

( * ) Notice: Subject to any disclaimer, the term of this patent is extended or adjusted under 35 U.S.C. 154(b) by 189 days.

(21) Appl. No.: 16/133,359

(22) Filed: Sep. 17, 2018

(65) Prior Publication Data

US 2019/0070085 A1 Mar. 7, 2019

Related U.S. Application Data

(63) Continuation of application No. PCT/US2018/049302, filed on Sep. 3, 2018.

(60) Provisional application No. 62/676,170, filed on May 24, 2018, provisional application No. 62/553,450, filed on Sep. 1, 2017.

(51) Int. Cl.
*A61K 8/44* (2006.01)
*A61K 8/20* (2006.01)
*A61K 8/21* (2006.01)
*A61K 8/24* (2006.01)
*A61Q 11/00* (2006.01)

(52) U.S. Cl.
CPC .............. *A61K 8/442* (2013.01); *A61K 8/20* (2013.01); *A61K 8/21* (2013.01); *A61K 8/24* (2013.01); *A61Q 11/00* (2013.01)

(58) Field of Classification Search
CPC ... A61K 8/21; A61K 8/24; A61K 8/20; A61K 8/442; A61K 2800/92; A61K 8/216; A61K 8/042; A61K 8/22; A61Q 11/00; A61Q 19/00; A61Q 17/005; A23V 2200/312; A61P 1/02; A61P 15/02; A61P 17/02; A61P 19/00; A61P 31/02; A61P 31/04; A61P 43/00
See application file for complete search history.

(56) References Cited

U.S. PATENT DOCUMENTS

| | | |
|---|---|---|
| 2,451,897 A | 10/1948 | Woodward |
| 2,482,891 A | 9/1949 | Mathieson |
| 3,271,242 A | 9/1966 | McNicholas et al. |
| 4,084,747 A | 4/1978 | Alliger |
| 4,330,531 A | 5/1982 | Alliger |
| 4,420,471 A | 12/1983 | Elton |
| 4,499,077 A | 2/1985 | Stockel et al. |
| 4,552,679 A | 11/1985 | Schobel et al. |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ratcliff |
| 4,851,213 A | 7/1989 | Ratcliff |
| 4,855,135 A | 8/1989 | Ratcliff |
| 4,861,514 A | 8/1989 | Hutchings |
| 4,886,657 A | 12/1989 | Ratcliff |
| 4,889,714 A | 12/1989 | Ratcliff |
| 4,891,216 A | 1/1990 | Kross et al. |
| 4,902,498 A | 2/1990 | Agricola et al. |
| 4,925,656 A | 5/1990 | Ratcliff |
| 4,963,346 A | 10/1990 | Amer |

(Continued)

FOREIGN PATENT DOCUMENTS

| | | |
|---|---|---|
| EP | 0613678 | 9/1994 |
| ES | 2079325 | * 1/1996 |

(Continued)

OTHER PUBLICATIONS

USPTO; Non-Final Office Action dated Aug. 20, 2008 in U.S. Appl. No. 11/774,730.

(Continued)

*Primary Examiner* — Lezah Roberts

(74) *Attorney, Agent, or Firm* — Snell & Wilmer L.L.P.

(57) ABSTRACT

Some embodiments described herein provide for a multi-component compositions and methods for its pharmaceutical and cosmetic use, comprising a combination of an aliphatic anionic compound, an oxidative compound, and a buffering system. Source of fluoride ion and other carriers are optional ingredients. The aliphatic anionic compound and the oxidative compound function together, in presence or absence of fluoride ion source, to protect the oxidative compounds from degradation prior to use and upon use, and to enhance the efficacy of the composition. In addition to achieving greater stability, combined effects of the aliphatic anionic compound, oxidative compound and source of fluoride ion achieve enhanced fluoride uptake, higher enamel protection by enhanced remineralization and reduced demineralization, increased plaque removal, reduced re-growth of plaque polymicrobial biofilm, greater amount of chlorite ion availability and effective oxidation of salivary biomolecules.

19 Claims, 4 Drawing Sheets

(56) References Cited

U.S. PATENT DOCUMENTS

| | | | |
|---|---|---|---|
| 4,975,285 A | 12/1990 | Ratcliff | |
| 5,192,691 A | 3/1993 | Quinn et al. | |
| 5,200,171 A | 4/1993 | Ratcliff | |
| 5,281,412 A | 1/1994 | Lukacovic et al. | |
| 5,284,648 A | 2/1994 | White et al. | |
| 5,348,734 A | 9/1994 | Ratcliff | |
| 5,364,462 A | 11/1994 | Crystal et al. | |
| 5,389,384 A | 2/1995 | Jooste | |
| 5,489,435 A | 2/1996 | Ratcliff | |
| 5,531,982 A | 7/1996 | Gaffar et al. | |
| 5,616,347 A | 4/1997 | Alliger et al. | |
| 5,618,550 A | 4/1997 | Ratcliff | |
| 5,667,817 A | 9/1997 | Kross | |
| 5,707,975 A | 1/1998 | Francois et al. | |
| 5,738,840 A | 4/1998 | Richter | |
| 5,772,986 A | 6/1998 | Kross | |
| 5,811,115 A | 9/1998 | Ratcliff | |
| 5,834,003 A | 11/1998 | Ratcliff | |
| 5,902,575 A | 5/1999 | Ratcliff | |
| 5,935,592 A | 8/1999 | Ratcliff | |
| 6,017,554 A | 1/2000 | Ratcliff | |
| 6,039,934 A | 3/2000 | Alliger | |
| 6,077,502 A | 6/2000 | Witt et al. | |
| 6,106,293 A | 8/2000 | Wiesel et al. | |
| 6,132,702 A | 10/2000 | Witt et al. | |
| 6,136,348 A | 10/2000 | Ratcliff et al. | |
| 6,231,830 B1 | 5/2001 | Madray | |
| 6,235,269 B1 | 5/2001 | Witt et al. | |
| 6,251,372 B1 | 6/2001 | Witt et al. | |
| 6,264,924 B1 | 7/2001 | Witt et al. | |
| 6,280,716 B1 | 8/2001 | Ratcliff | |
| 6,280,775 B1 | 8/2001 | Sasson et al. | |
| 6,291,166 B1 | 9/2001 | Gerdes et al. | |
| 6,325,997 B1 | 12/2001 | Christopfel | |
| 6,350,438 B1 | 2/2002 | Witt et al. | |
| 6,375,933 B1 | 4/2002 | Subramanyam | |
| 6,391,577 B1 | 5/2002 | Mikkelsen et al. | |
| 6,582,682 B2 | 6/2003 | Stier | |
| 6,696,047 B2 | 2/2004 | Scott et al. | |
| 6,780,838 B2 | 8/2004 | Lipton et al. | |
| 6,846,478 B1 | 1/2005 | Doyle et al. | |
| 7,087,228 B2 | 8/2006 | Goodman | |
| 7,387,774 B2 | 6/2008 | Faller et al. | |
| 7,737,166 B2 | 6/2010 | Kawakami et al. | |
| 8,252,771 B2 | 8/2012 | Uecht et al. | |
| 8,697,141 B2 | 4/2014 | Ratcliff | |
| 8,906,348 B2 | 12/2014 | Narasimhan et al. | |
| 8,926,951 B2 | 1/2015 | Ratcliff | |
| 8,980,229 B2 * | 3/2015 | Pilch | A61K 8/19 424/49 |
| 9,682,023 B2 | 6/2017 | Ratcliff | |
| 9,937,204 B2 | 4/2018 | Young et al. | |
| 2001/0006624 A1 * | 7/2001 | Witt | A61K 8/20 424/53 |
| 2002/0028324 A1 | 3/2002 | Koichi et al. | |
| 2002/0197215 A1 | 12/2002 | Stier | |
| 2003/0066336 A1 | 4/2003 | Kotsuka et al. | |
| 2003/0129144 A1 | 7/2003 | Scott | |
| 2005/0084551 A1 | 4/2005 | Jensen et al. | |
| 2005/0196370 A1 | 9/2005 | Yu et al. | |
| 2005/0234545 A1 | 10/2005 | Su et al. | |
| 2007/0190176 A1 | 8/2007 | Percival et al. | |
| 2008/0055154 A1 | 3/2008 | Martucci et al. | |
| 2008/0247973 A1 | 10/2008 | Baig et al. | |
| 2008/0269353 A1 | 10/2008 | Takada et al. | |
| 2009/0016973 A1 | 1/2009 | Ratcliff | |
| 2010/0009009 A1 | 1/2010 | Young et al. | |
| 2010/0015207 A1 | 1/2010 | Speronello et al. | |
| 2010/0036305 A1 * | 2/2010 | Green | A01N 25/16 602/43 |
| 2010/0221198 A1 | 9/2010 | Ratcliff | |
| 2010/0233101 A1 | 9/2010 | Grootveld et al. | |
| 2011/0318282 A1 | 12/2011 | Ratcliff et al. | |
| 2012/0034280 A1 | 2/2012 | Cohen et al. | |
| 2012/0164084 A1 | 6/2012 | Ratcliff et al. | |
| 2012/0201899 A1 | 8/2012 | McWhorter et al. | |
| 2015/0017107 A1 | 1/2015 | Hill | |
| 2015/0297478 A1 | 10/2015 | Ratcliff | |
| 2017/0216351 A1 | 8/2017 | Young et al. | |
| 2017/0319877 A1 | 11/2017 | Grootveld et al. | |

FOREIGN PATENT DOCUMENTS

| | | |
|---|---|---|
| JP | S6054311 | 3/1985 |
| WO | 2003022256 | 3/2003 |
| WO | 2009009162 | 1/2009 |
| WO | 2009009163 | 1/2009 |
| WO | 2011119177 | 6/2010 |
| WO | 2012051727 | 4/2012 |
| WO | 2019046841 | 3/2019 |

OTHER PUBLICATIONS

USPTO; Final Office Action dated Mar. 3, 2009 in U.S. Appl. No. 11/774,730.

USPTO; Advisory Action dated Jul. 10, 2009 in U.S. Appl. No. 11/774,730.

USPTO; Non-Final Office Action dated Nov. 9, 2009 in U.S. Appl. No. 11/774,730.

USPTO; Non-Final Office Action dated Feb. 22, 2010 in U.S. Appl. No. 11/774,789.

USPTO; Final Office Action dated Jun. 29, 2010 in U.S. Appl. No. 11/774,730.

USPTO; Notice of Allowance dated Sep. 29, 2010 in U.S. Appl. No. 11/774,789.

USPTO; Advisory Action dated Dec. 17, 2010 in U.S. Appl. No. 11/774,730.

USPTO; Restriction Requirement dated Dec. 28, 2010 in U.S. Appl. No. 12/500,163.

USPTO; Non-Final Office Action dated Jan. 27, 2011 in U.S. Appl. No. 12/500,163.

USPTO; Restriction Requirement dated Apr. 29, 2011 in U.S. Appl. No. 12/547,420.

USPTO; Non-Final Office Action dated May 31, 2011 in U.S. Appl. No. 12/547,420.

USPTO; Non-Final Office Action dated Jul. 19, 2011 in U.S. Appl. No. 11/774,730.

USPTO; Final Office Action dated Feb. 13, 2012 in U.S. Appl. No. 12/547,420.

USPTO; Final Office Action dated Mar. 23, 2012 in U.S. Appl. No. 11/774,730

USPTO; Advisory Action dated Jul. 19, 2012 in U.S. Appl. No. 12/547,420.

USPTO; Advisory Action dated Oct. 17, 2012 in U.S. Appl. No. 11/774,730.

USPTO; Non-Final Office Action dated Jun. 20, 2013 in U.S. Appl. No. 11/774,730.

USPTO; Final Office Action dated Nov. 27, 2013 in U.S. Appl. No. 11/774,730.

USPTO; Notice of Allowance dated Dec. 2, 2013 in U.S. Appl. No. 12/547,420.

USPTO; Advisory Action dated Apr. 1, 2014 in U.S. Appl. No. 11/774,730.

USPTO; Advisory Action dated Jun. 3, 2014 in U.S. Appl. No. 11/774,730.

USPTO; Non-Final Office Action dated Nov. 28, 2014 in U.S. Appl. No. 11/774,730.

USPTO; Final Office Action dated May 4, 2015 in U.S. Appl. No. 11/774,730.

USPTO; Advisory Action dated Aug. 24, 2015 in U.S. Appl. No. 11/774,730.

USPTO; Non-Final Office Action dated Oct. 7, 2015 in U.S. Appl. No. 11/774,730.

USPTO; Non-Final Office Action dated Jan. 22, 2018 in U.S. Appl. No. 11/774,730.

USPTO; Non-Final Office Action dated May 26, 2011 in U.S. Appl. No. 12/704,360.

(56) References Cited

OTHER PUBLICATIONS

USPTO; Final Office Action dated Oct. 19, 2011 in U.S. Appl. No. 12/500,163.
USPTO; Final Office Action dated Dec. 2, 2011 in U.S. Appl. No. 12/704,360.
USPTO; Advisory Action dated Mar. 5, 2012 in U.S. Appl. No. 12/500,163.
USPTO; Non-Final Office Action dated Dec. 19, 2012 in U.S. Appl. No. 12/704,360.
USPTO; Restriction Requirement dated Sep. 14, 2011 in U.S. Appl. No. 12/731,271.
USPTO; Non-Final Office Action dated Oct. 19, 2011 in U.S. Appl. No. 12/731,271.
USPTO; Final Office Action dated Jan. 9, 2014 in U.S. Appl. No. 12/731,271.
USPTO; Advisory Action dated Apr. 1, 2014 in U.S. Appl. No. 12/731,271.
USPTO; Notice of Allowance dated Nov. 3, 2014 in U.S. Appl. No. 12/731,271.
USPTO; Restriction Requirement dated Feb. 28, 2013 in U.S. Appl. No. 13/115,815.
USPTO; Non-Final Office Action dated Jun. 4, 2013 in U.S. Appl. No. 13/115,815.
USPTO; Final Office Action dated Mar. 13, 2014 in U.S. Appl. No. 13/115,815
USPTO; Advisory Action dated Jul. 24, 2014 in U.S. Appl. No. 13/115,815.
USPTO; Non-Final Office Action dated Apr. 24, 2015 in U.S. Appl. No. 13/115,815.
USPTO; Final Office Action dated Nov. 20, 2015 in U.S. Appl. No. 13/115,815.
USPTO; Restriction Requirement dated Mar. 28, 2013 in U.S. Appl. No. 13/131,506.
USPTO; Restriction Requirement dated Apr. 22, 2013 in U.S. Appl. No. 13/131,506.
USPTO; Final Office Action dated Aug. 26, 2013 in U.S. Appl. No. 12/704,360.
USPTO; Non-Final Office Action dated Jan. 24, 2014 in U.S. Appl. No. 12/500,163.
USPTO; Advisory Action dated Feb. 12, 2014 in U.S. Appl. No. 12/704,360.
USPTO; Non-Final Office Action dated Apr. 10, 2014 in U.S. Appl. No. 12/704,360.
USPTO; Non-Final Office Action dated May 22, 2014 in U.S. Appl. No. 13/131,506.
USPTO; Final Office Action dated Jul. 31, 2014 in U.S. Appl. No. 12/500,163.
USPTO; Final Office Action dated Oct. 22, 2014 in U.S. Appl. No. 12/704,360.
USPTO; Advisory Action dated Nov. 13, 2014 in U.S. Appl. No. 12/500,163.
USPTO; Advisory Action dated Mar. 6, 2015 in U.S. Appl. No. 12/704,360.
USPTO; Non-Final Office Action dated Mar. 12, 2015 in U.S. Appl. No. 12/500,163.
USPTO; Non-Final Office Action dated Jun. 18, 2015 in U.S. Appl. No. 12/704,360.
USPTO; Final Office Action dated Aug. 6, 2015 in U.S. Appl. No. 12/500,163.
USPTO; Restriction Requirement dated Oct. 8, 2015 in U.S. Appl. No. 14/145,426.
USPTO; Advisory Action dated Nov. 13, 2015 in U.S. Appl. No. 12/500,163.
USPTO; Final Office Action dated Dec. 10, 2015 in U.S. Appl. No. 12/704,360.
USPTO; Final Office Action dated Dec. 17, 2015 in U.S. Appl. No. 13/131,506.
USPTO; Non-Final Office Action dated Jan. 29, 2016 in U.S. Appl. No. 12/500,163.
USPTO; Non-Final Office Action dated Mar. 24, 2016 in U.S. Appl. No. 12/704,360.
USPTO; Advisory Action dated Apr. 21, 2016 in U.S. Appl. No. 13/131,506.
USPTO; Non-Final Office Action dated May 20, 2016 in U.S. Appl. No. 14/145,426.
USPTO; Non-Final Office Action dated Jul. 26, 2016 in U.S. Appl. No. 14/589,260
USPTO; Final Office Action dated Sep. 30, 2016 in U.S. Appl. No. 12/500,163.
USPTO; Final Office Action dated Nov. 25, 2016 in U.S. Appl. No. 12/704,360.
USPTO; Non-Final Office Action dated Dec. 23, 2016 in U.S. Appl. No. 13/131,506.
USPTO; Non-Final Office Action dated Aug. 11, 2015 in U.S. Appl. No. 14/192,195.
USPTO; Final Office Action dated Jan. 7, 2016 in U.S. Appl. No. 14/192,195.
USPTO; Advisory Action dated Apr. 20, 2016 in U.S. Appl. No. 14/192,195.
USPTO; Non-Final Office Action dated Jun. 16, 2016 in U.S. Appl. No. 14/192,195.
USPTO; Notice of Allowance dated Feb. 16, 2017 in U.S. Appl. No. 14/589,260.
USPTO; Non-Final Office Action dated May 18, 2017 in U.S. Appl. No. 15/475,006.
USPTO; Final Office Action dated Nov. 1, 2017 in U.S. Appl. No. 13/131,506.
USPTO; Final Office Action dated Jun. 6, 2018 in U.S. Appl. No. 11/774,730.
USPTO; Non-Final Office Action dated Jun. 14, 2018 in U.S. Appl. No. 15/605,506.
USPTO; Notice of Allowance dated Nov. 27, 2017 in U.S. Appl. No. 15/475,006.
PCT; International Search Report dated Feb. 27, 2008 in International Application No. PCT/US2008/55154.
PCT; Written Opinion dated Jun. 26, 2008 in International Application No. PCT/US2008/55154.
PCT; International Preliminary Report on Patentability dated Aug. 25, 2009 in International Application No. PCT/US2008/55154.
PCT; Written Opinion dated Jul. 30, 2010 in International Application No. PCT/US2010/37768.
PCT; International Search Report dated Jul. 30, 2010 in International Application No. PCT/US2010/37768.
JPO; Office Action dated Dec. 21, 2012 in Japanese Application No. 2010-516078.
JPO; Office Action dated Jun. 19, 2013 in Japanese Application No. 2010-516078.
JPO; Report of Pretrial Reconsideration dated Dec. 12, 2013 in Japanese Application No. 2010-516078.
JPO; Office Action dated Nov. 11, 2014 in Japanese Application No. 2013-217385.
JPO; Office Action dated Aug. 17, 2015 in Japanese Application No. 2013-217385.
JPO; Office Action dated Apr. 4, 2016 in Japanese Application No. 2013-217385.
3M, "Material Safety Data Sheet," Peridex CHG 0.12% Oral Rinse; MSDS No. 25-8627-9 [Online]; 3M: St Paul, MN, http://library.queensu.ca/research/guide/how-cite-chemical-literature/material-safety-data-sheets, (2011).
Aas, JA. et al., "Defining the Normal Bacterial Flora of the Oral Cavity," Journal of Clinical Microbiology, vol. 43(11), pp. 5721-5732, (2005).
Abu-Elteen et al., "The Prevalence of *Candida albicans* Populations in the Mouths of Complete Denture Wearers," The New Microbiologica, vol. 21, pp. 41-48, (1998).
American Dental Association, "Fluoridation Facts," 72 Pages, (2005 Edition).
Armitage, "Clinical Evaluation of Periodontal Diseases," Periodontology 2000, vol. 7, pp. 39-53, (1995).
Aoba et al., "Dental Fluorosis: Chemistry and Biology," Critical Reviews in Oral Biology & Medicine, vol. 13, pp. 155-170, (2002).

(56) References Cited

OTHER PUBLICATIONS

Baehni et al., "Anti-Plaque Agents in the Prevention of Biofilm-Associated Oral Diseases," Oral Diseases, vol. 9(1), pp. 23-29, (2003).
Barnhart et al., "Dentifrice Usage and Ingestion Among Four Age Groups," Journal of Dental Research, vol. 53(6), pp. 1317-1322, (1974).
Bagg et al., "Voriconazole Susceptibility of Yeasts Isolated from the Mouths of Patients with Advanced Cancer," Journal of Medical Microbiology, vol. 54, pp. 959-964, (2005).
Bassani et al., "Periodontal Disease and Perinatal Outcomes: A Case-Control Study," Journal of Clinical Periodontology, vol. 34, pp. 31-39, (2007).
Barkvoll et al., "Interaction Between Chlorhexidine Digluconate and Sodium Monofluorophosphate in Vitro," Scand. Journal of Dental Research, vol. 96(1), (1988). (Abstract Only).
Beck et al., "Periodontal Disease and Cardiovascular Disease," Journal of Periodontology, vol. 67, pp. 1123-1137, (1996).
Benarde et al., "Kinetics and Mechanism of Bacterial Disinfection by Chlorine Dioxide," Applied Microbiology, vol. 15(2), pp. 257-265, (1967).
Berg et al., "Effect of Chlorine Dioxide on Selected Membrane Functions of *Escherichia coli*," Journal of Applied Bacteriology, vol. 60, pp. 213-220, (1986).
Blignaut, "Oral Candidiasis and Oral Yeast Carriage Among Institutionalized South African Paediatric HIV/AIDS Patients," Mycopathologia vol. 163, pp. 67-73, (2007).
Boggess et al., "Fetal Immune Response to Oral Pathogens and Risk of Preterm Birth," American Journal of Obstetrics and Gynecology, vol. 193, pp. 1121-1126, (2005).
Bolstad et al., "Taxonomy, Biology, and Periodontal Aspects of *Fusobacterium nucleatum*," Clinical Microbiology Reviews, vol. 9(1), pp. 55-71, (1996).
Botha et al., "Effective Inhibition of Oral Organisms by Chlorine Dioxide ($ClO_2$)," The Preliminary Program for Scientific Meeting of the South African Division of IADR, (2006).
Bouillaguet, "Biological Risks of Resin-Based Materials to the Dentin-Pulp Complex," Critical Reviews in Oral Biology & Medicine, vol. 15(1), pp. 47-60, (2004).
Braly et al., "The Effect of Prism Orientation in the Indentation Testing of Human Molar Enamel," Archives of Oral Biology, vol. 52(9), pp. 856-860, (2007).
Brand et al., "Effect of a Protein-Rich Meal on Urinary and 2 Salivary Free Amino Acid Concentrations in Human Subjects," Clinica Chimica Acta, vol. 264(1), pp. 37-47, abstract (1 page), (1997).
Briggs et al., "Angiographically Confirmed Coronary Heart Disease and Periodontal Disease in Middle-Aged Males," Journal of Periodontology, vol. 77(1), pp. 95-102, (2006).
Buduneli et al., "Periodontal Infections and Pre-Term Low Birth Weight: A Case-Control Study," Journal of Clinical periodontology, vol. 32, pp. 174-181, (2005).
Campisi et al., "Candidal Carriage in the Oral Cavity of Human Immunodeficiency Virus-Infected Subjects," Oral Surgery, Oral Medicine, Oral Pathology, Oral Radiology, and Endodontology, vol. 93, pp. 281-286, (2002).
Canton et al., "Minimum Fungicidal Concentrations of Amphotericin B for Bloodstream *Candida* Species," Diagnostic Microbiology and Infectious Disease, vol. 45, pp. 203-206, (2003).
Cartledge et al., "Non-Albicans Oral Candidosis in HIV-Positive Patients," Journal of Antimicrobial Chemotherapy, vol. 43, pp. 419-422, (1999).
Caie et al., "Molecular and Cellular Mechanisms That Lead to Candida Biofilm Formation," Journal of Dental Research, vol. 88(2), pp. 105-115, (2009).
Challacombe, "Immunologic Aspects of Oral Candidiasis," Oral Surgery, Oral Medicine, Oral Pathology, vol. 78, pp. 202-210, (1994).
Chang et al., "High-Resolution (1) H NMR Investigations of the Oxidative Consumption of Salivary Biomolecules by Oral Rinse Peroxides," Acta Odontologia Scandanivica, (2012). (Abstract only).
Chang et al., "1H NMR Investigations of the Molecular Nature of Cobalt (II) Ions in Human Saliva," Archives of Biochemistry and Biophysics, vol. 520(1), pp. 51-65, (2012). (Abstract only).
Chapek et al., "Management of Periodontitis with Oral-Care Products," Compendium of Continuing Education in Dentistry, vol. 15(6), pp. 740-746, (1994).
Chattopadhyay et al., "Risk Indicators for HIV-Associated Jointly Occurring Oral Candidiasis and Oral Hairy Leukoplakia," AIDS Patient Care and STDs, vol. 21(11), pp. 825-832, (2007).
Chattopadhyay et al., "Risk Indicators for Oral Candidiasis and Oral Hairy Leukoplakia in HIV-Infected Adults," Community Dentistry and Oral Epidemiology, vol. 33, pp. 35-44, (2005).
Chattopadhyay et al., "Incidence of Oral Candidiasis and Oral Hairy Leukoplakia in HIV-Infected Adults in North Carolina," Oral Surgery, Oral Medicine, Oral Pathology, Oral Radiology, and Endodontology, vol. 99(1), pp. 39-47, (2005).
Chinake et al., "Oxidation of Formaldehyde by Chlorite in Basic and Slightly Acidic Media," Journal of Physical Chemistry, vol. 102, pp. 606-611, (1998).
Chinake et al., "Oxyhalogen-Sulfur Chemistry: Oxidation of Taurine by Chlorite in Acidic Medium," Journal of Physical Chemistry B, vol. 101, pp. 1207-1214, (1997).
CLSI, "Reference Method for Broth Dilution Antifungal Susceptibility Testing of Yeasts," Approved Standard—Second Edition, vol. 22(15), 15 Pgs., (2002).
Coleman et al., "Candidiasis: The Emergence of a Novel Species, *Candida dubliniensis*" AIDS, vol. 11(5), pp. 557-567, (1997).
Conley et al., "The Association Between Cigarette Smoking and Selected HIV-Related Medical Conditions," AIDS, vol. 10, pp. 1121-1126, (1996).
Coogan et al., "(B1) Candida and Mycotic Infections," Advances in Dental Research, vol. 19, pp. 130-138, (2006).
Corbin et al., "Antimicrobial Penetration and Efficacy in an In Vitro Oral Biofilm Model," Antimicrobial Agents and Chemotherapy, vol. 55(7), pp. 3338-3344, (2011).
Cury et al., "Enamel Remineralization: Controlling the Caries Disease or Treating Early Caries Lesions," Braz. Oral Research, vol. 23(1), pp. 23-30, (2009).
Cury et al., "How To Maintain a Cariostatic Fluoride Concentration in the Oral Environment," Advances in Dental Research, vol. 20, pp. 13-16, (2008).
Daily Med: "Current Medication Information. Chlorhexidine Gluconate Rinse [Xttrium Laboraories, Inc.]," Available at: http://dailymed.nlm.nih.gov/dailymed/lookup.cfm?setid=34d15e72-8770-49dc-a514-d44ae4468a1e, (2010).
Daily Med: "Current Medication Information. Periogard (Chlorhexidine Gluconate) Liquid [Colgate-Palmolive Company]," Available at: http://dailymed.nlm.nih.gov/dailymed/lookup.cfm?setid=6e537d5f-bce1-41ce-9984-9b3c2861b7c9, (2010).
Daniel et al., "Comparative Subchronic Toxicity Studies of Three Disinfectants," Journal of the American Water Works Association, vol. 10, pp. 61-69, (1990).
Darkwa et al., "Oxyhalogen-Sulfur Chemistry: Oxidation of N-Acetylcysteine by Chlorite and Acidic Bromate," The Journal of Physical Chemistry A, vol. 107(46), pp. 9834-9845, (2003).
Davies et al., "Oral Candidosis in Patients with Advanced Cancer," Oral Oncology, vol. 42, pp. 698-702, (2006).
Denes et al., "Oxidation of $SnF_2$ Stannous Fluoride in Aqueous Solutions," Hyperfine Interactions, vol. 90(1), pp. 435-439, (1994). (Abstract Only).
Drake, "Final Report: Phase III Biofilm Studies," Rowpar Pharmaceuticals, Inc., 12 Pages, (2008).
Edgar et al., "Role of Saliva in Caries Models," Advances in Dental Research, vol. 9(3), pp. 235-238, (1995).
Emilson et al., "Effect of a Fluoride-Containing Chlorhexidine Gel on Bacteria in Human Plaque," Scand. Journal of Dental Research, vol. 84(2), (1976). (Abstract Only).

(56) References Cited

OTHER PUBLICATIONS

European Commission, Enterprise Directorate-General, The Rules Governing Cosmetic Products in the European Union, Cosmetics Legislation, "Cosmetic Products," 1999 Edition, vol. 1, 3 Pgs., (1999).
Featherstone, "Carries Prevention and Reversal Based on the Carries Balance," Pediatric Dentistry, vol. 28(2), pp. 128-132, (2006).
Featherstone, "Delivery Challenges for Fluoride, Chlorhexidine and Xylitol," BMC Oral Health, vol. 6(Supp 8), 5 Pgs., (2006).
Final Report: Study No. 1439, "The Effect of Experimental Oral Care Products on Carries Formation in the Rat," 18 Pgs., (2008).
Final Report: EFU-R-0701, "Fluoride Uptake in Incipient Enamel Lesions After Dentifrice Treatment (FDA Test #40)," 4 Pgs., (2007).
Food and Drug Administration, "Anticaries Drug Products for Over-the-Counter Human Use: Final Monograph," Title 21, Federal Register, vol. 60, No. 194, Parts 310, 355, and 369, 2 Pgs., (1995).
Food and Drug Administration, "Guidance for Industry Q1A(R2) Stability Testing of New Drug Substances and Products," US Department of Health and Human Services, Revision 2, 25 Pgs., (2003).
Ford et al., "Cross-Reactivity of GroEL Antibodies with Human Heat Shock Protein 60 and Quantification of Pathogens in Atherosclerosis," Oral Microbiology Immunology, vol. 20, pp. 296-302, (2005).
Ford et al., "Anti-P Gingivalis Response Correlates with Atherosclerosis," Journal of Dental Research, vol. 86(1), pp. 35-40, (2007).
Frascella et al., "Odor Reduction Potential of a Chlorine Dioxide Mouthrinse," Journal of Clinical Dentistry, vol. 9(2), pp. 39-42, (1998).
Freitas et al., "Evaluation of the Substantivity of Chlorhexidine in Association with Sodium Fluoride in Vitro," Pesqui Odontologica Brasileira, vol. 17(1), pp. 78-81, (2003).
Frontier Pharmaceutical Inc., "The DioxiCare System," http://www.frontierpharm.com/dioxicare-system.php, 5 Pages, (2008).
Garcia et al., "Relationship Between Periodontal Disease and Systemic Health," Periodontology 2000, vol. 25, pp. 21-36, (2001).
Garcia-Godoy et al, "Maintaining the Integrity of the Enamel Surface: The Role of Dental Biofilm, Saliva, and Preventive Agents in Enamel Demineralization and Remineralization," Journal of American Dentistry Association, vol. 139, pp. 25S-34S, (2008).
Goncalves et al., "Species Diversity of Yeast in Oral Colonization of Insulin-Treated Diabetes Mellitus Patients," Mycopathologia, vol. 162, pp. 83-89, (2006).
Gonzalez-Gravina et al., "Oral Candidiasis in Children and Adolescents with Cancer, Identification of *Candida* SPP," Medicina Oral, Patologia Oral y Cirugia Bucal, vol. 12(6), pp. E419-E423, (2007).
Grau et al., "Periodontal Disease as a Risk Factor for Ischemic Stroke," Stroke: Journal of the American Heart Association, vol. 35(2), pp. 496-501, (2004).
Grootveld et al., "Evidence for the Microbicidal Activity of a Chlorine Dioxide-Containing Oral Rinse Formulation In Vivo," Journal of Clinical Dentistry, vol. 12(3), pp. 67-70, (2001).
Grootveld et al., "H NMR-Linked Chemometric Analysis of Control and Dentifrice-Treated Human Saliva," IADR/AADR/CADR 87th General Session and Exhibition, (2009). (Abstract Only).
Gudlauggson et al., "Attributable Mortality of *Nosocomial candidemia*, Revisited," Clinical Infectious Diseases, vol. 37, pp. 1172-1177, (2003).
Gunsolley, "A Meta-Analysis of Six-Month Studies of Antiplaque and Antigingivitis Agents," Journal of American Dental Association, vol. 137, pp. 1649-1657, (2006).
Hajjeh et al., "Incidence of Bloodstream Infections Due to *Candida* Species and In Vitro Susceptibilities of Isolates Collected from 1998 to 2000 in a Population-Based Active Surveillance Program," Journal of Clinical Microbiology, vol. 42(4), pp. 1519-1527, (2004).
Han et al., "*Fusobacterium nucleatum* Induces Premature and Term Stillbirths in Pregnant Mice: Implication of Oral Bacterial in Preterm Birth," Infection and Immunity, vol. 72(4), pp. 2272-2279, (2004).

Harakeh et al., "Inactivation of Bacteria by Purogene," Journal of Applied Bacteriology, vol. 64(5), pp. 459-463, (1988). (Abstract Only).
Hazen et al., "Human Neutrophils Employ the Myeloperoxidase-Hydrogen Peroxide-Chloride System to Oxidize Alpha-Amino Acids to a Family of Reactive Aldehydes: Mechanistic Studies Identifying Labile Intermediates Along the Reaction Pathway," Journal of Biological Chemistry, vol. 273(9), pp. 4997-5005, (1998).
Herzberg et al., "Dental Plaque, Platelets, and Cardiovascular Diseases," Annals of Periodontology, vol. 3, pp. 151-160, (1998).
Hojo et al., "Bacterial Interaction in Dental Biofilm Development," Journal of Dental Research, vol. 88(11), pp. 982-990, (2009).
Holt et al., "*Porphyromonas gingivalis, Treponema denticola*, and *Tannerella forsythis*: The Red Complex, A Prototype Polybacterial Pathogenic Consortium in Periodontitis," Periodontology 2000, vol. 38, pp. 72-122, (2005).
"Ingredients: Tetrasodium Pryophosphate," http://sci-toys.com/ingredients/tetrasodium_pyrophosphate.html, 2 Pgs., (2011).
International Conference on Harmonisation of Technical Requirements for Registration of Pharmaceuticals for Human Use (ICH), "Guidance for Industry Q1A(R2) Stability Testing of New Drug Substances and Products," 24 Pgs., (2003).
Islam et al., "Dental Caries: From Infection to Prevention," Medical Science Monitor, vol. 13(11), pp. 196-203, (2007).
Jacobsen et al., "Mixed *Candida albicans* Strain Populations in Colonized and Infected Mucosal Tissues," Federation of European Microbiological Societies Yeast Research, vol. 8, pp. 1334-1338, (2008).
Spratt et al., "Dental Plaque and Bacterial Colonization," Medical Biofilms, Chapter 4.1, pp. 173-198, (2003).
Kazor et al., "Diversity of Bacterial Populations on the Tongue Dorsa of Patients with Halitosis and Healthy Patients," Journal of Clinical Microbiology, vol. 41(2), pp. 558-563, (2003).
Keyes, "Dental Caries in the Molar Teeth of Rats: II. A Method for Diagnosing and Scoring Several Types of Lesions Simultaneously," Journal of Dental Research, vol. 37(6), pp. 1088-1099, (1958).
Kidd et al., "What Constitutes Dental Caries? Histopathology of Carious Enamel and Dentin Related to the Action of Cariogenic Biofilms," Journal of Dental Research, vol. 83, pp. C35-C38, (2004).
Kim et al., "Periodontal Disease and Systemic Conditions: A Bi-Directional Relationship," Odontology, vol. 94, pp. 10-21, (2006).
Kirsch, "Final Report: The Evaluation of Chlorine Dioxide Dentifrice Formulations," University of Iowa, pp. 1-90, (2006).
Kleinberg et al., "The pH of Dental Plaques in the Different Areas of the Mouth Before and After Meals and Their Relationship to the pH and Rate of the Flow of Resting Saliva," Archives of Oral Biology, vol. 9, pp. 493-516, (1964).
Kolahi et al., "Rinsing With Chlorhexidine Gluconate Solution After Brushing and Flossing Teeth: A Systematic Review of Effectiveness," Quintessence Int., vol. 37(8), pp. 605-612, (2006). (Abstract Only).
Krishnaraju et al., "Comparative Genomics and Structure Prediction of Dental Matrix Proteins," Advances in Dental Research, vol. 17, pp. 100-103, (2003).
Kubota et al., "Efficacy of Chlorine Dioxide: Gas against *Porphyromonas gingivalis*, Nihon Koku Implant Gakkai Shi," Japanese Society of Oral Implantology, vol. 18(2), pp. 222-228, (2005).
Lee et al., "Cytotoxicity of Chlorhexidine on Human Osteoblastic Cells is Related to Intracellular Glutathione Levels," International Endodontic Journal, vol. 43(5), pp. 430-435, (2010).
Lendenmann et al., "Saliva and Dental Pellicle—A Review," Advances in Dental Research, vol. 14, pp. 22-28, (2000).
Leone et al., "Physical and Chemical Aspects of Saliva as Indicators of Risk for Dental Caries in Humans," Journal of Dental Education, vol. 65(10), pp. 1054-1062, (2001).
Lessa et al., "Toxicity of Chlorhexidine on Odontoblast-Like Cells," Journal of Applied Oral Science, vol. 18(1), pp. 50-58, (2010).
Levitt et al., "Antibiotics and Dental Biofilms," The Journal of Professional Excellence, Dimensions of Dental Hygiene, vol. 10, pp. 56-59, (2012).

(56) References Cited

OTHER PUBLICATIONS

Li et al., "*Candida glabrata*, An Emerging Oral Opportunistic Pathogen," Journal of Dental Research, vol. 86(3), pp. 204-215, (2007).
Lim et al., "Relationship Between Markers of Metabolic Control and Inflammation on Severity of Periodontal Disease in Patients with Diabetes Mellitus," Journal of Clinical Periodontal, vol. 34, pp. 118-123, (2007).
Lockhart et al., "Natural Defenses Against Candida Colonization Breakdown in the Oral Cavities of the Elderly," Journal of Dental Research, vol. 78(4), pp. 857-868, (1999).
Loesche et al., "Microbiology and Treatment of Halitosis," Periodontology 2000, vol. 28, pp. 256-279, (2002).
Lubbers et al., "The Effects of Chronic Administration of Chlorine Dioxide, Chlorite and Chlorate to Normal Healthy Adult Male Volunteers," Journal of Environmental Pathology, Toxicology and Oncology, vol. 5(4-5), pp. 229-238, (1984).
Luoma et al., "A Simultaneous Reduction of Caries and Gingivitis in a Group of Schoolchildren Receiving Chlorhexidine-Fluoride Applications, Results After 2 Years," Caries Research, vol. 12(5), 2 Pages, (1978).
Lynch et al., "Multicomponent Spectroscopic Investigations of Salivary Antioxidant Consumption by an Oral Rinse Preparation Containing the Stable Free Radical Species Chlorine Dioxide (ClO2)," Free Radical Research, vol. 26(3), pp. 209-234, (1997).
Madianos et al., "Maternal Periodontitis and Prematurity, Part II: Maternal Infection and Fetal Exposure," Annual Periodontology, vol. 6(1), pp. 175-182, (2001).
Marder et al., "Bisphosphonate-Associated Osteonecrosis: Experiences in a Private Practice," Dentistry Today, vol. 27(10), pp. 99-103, (2008).
Margolis et al., "Role of Macromolecular Assembly of Enamel Matrix Proteins in Enamel Formation," Journal of Dental Research, vol. 85, pp. 775-793, (2006).
Marsh, "Dental Plaque as a Microbial Biofilm," Caries Research, vol. 38, pp. 204-2011, (2004).
Marsh, "Dental Plaque: Biological Significance of a Biofilm and Community Life-Style," Journal of Clinical Periodontology, vol. 32, pp. 7-15, (2005).
Masschelein, "Chlorine Dioxide: Chemistry and Environmental Impact of Oxychlorine Compounds," Ann Arbor Science Publishers Inc., Ann Arbor, Michigan, pp. 153-156, (1979).
Masschelein, "Chlorine Dioxide: Chemistry and Environmental Impact of Oxychlorine Compounds," Ann Arbor Science Publishers Inc., Ann Arbor, Michigan, pp. 138-141, (1979).
Masschelein, "Chemical Oxidation: Technologies: Technologies for the Nineties," Lancaster Technomic Publishing Company, vol. 1, pp. 170-192, (1992).
McBain et al., "Effects of a Chlorhexidine Gluconate-Containing Mouthwash on the Vitality and Antimicrobial Susceptibility of In Vitro Oral Bacterial Ecosystems," Applied Environmental Microbiology, vol. 69(8), pp. 4770-4776, (2003).
McCarthy et al., "Factors Associated with Increased Frequency of HIV-Related Oral Candidiasis," Journal of Oral Pathology and Medicine, vol. 20, pp. 332-336, (1991).
Medical Subject Headings (MeSH), http://www.ncbi.nlm.nih.gov/mesh, National Library of Medicine, (2011).
The Merck Index: An Encyclopedia of Chemicals, Drugs, and Biologicals, 12th Edition, Whitehouse Station, NJ; Merck & Co. Inc., (1996).
The Merck Index: An Encyclopedia of Chemicals, Drugs, and Biologicals, 14th Edition, Whitehouse Station, NJ; Merck & Co. Inc., (2006).
Michael et al., "Chlorine Dioxide Water Disinfection: A Prospective Epidemiology Study," Archives of Environmental Health, vol. 36(1), pp. 20-27, (1981).
Michaud, "A Prospective Study of Periodontal Disease and Pancreatic Cancer in US Male Health Professionals," Journal of the National Cancer Institute, vol. 99(2), pp. 171-175, (2007).
Mjor, "Dentin Permeability: The Basis for Understanding Pulp Reactions and Adhesive Technology," Brazilian Dental Journal, vol. 20(1), pp. 3-16, (2009).
Mohammad et al., "Clinical and Microbiological Efficacy of Chlorine Dioxide in the Management of Chronic Atrophic Candidiasis: An Open Study," International Dental Journal, vol. 54(3), pp. 154-158, (2004).
Moran G.P., et al., "Antifungal Drug Susceptibilities of Oral *Candida dubliniensis* Isolates from Human Immunodeficiency Virus (HIV)-Infected and Non-HIV-Infected Subjects and Generation of Stable Fluconazole-Resistant Derivative In Vitro.," Antimicrobial Agents and Chemotherapy, vol. 41(3), pp. 617-623, (1997).
Moran et al., "Emergence of Non-*Candida albicans Candida* Species as Pathogens," R.A. Calderone (ed.), *Candida* and Candidaisis. Washington, DC: ASM Press, pp. 37-53, (2002).
Mullally et al., "Prevalence of Periodontal Pathogens in Localized and Generalized Forms of Early-Onset Periodontitis," Journal of Periodontal Research, vol. 35, pp. 232-241, (2000).
Nase et al., "Osteonecrosis of the Jaw and Oral Bisphosphonate Treatment," Journal of the American Dental Association, vol. 137, pp. 1115-1119, (2006).
USP, "New or Revised Standards," http://www.usp.org/get-involved/partner/new-revised-standars, 2 Pages, (2017).
Nguyen et al., "Common Dental Infections in the Primary Care Setting," American Family Physician, vol. 77(6), pp. 797-802, (2008).
Nishimura et al., "The Periodontal Host Response with Diabetes," Periodontology 2000, vol. 43, pp. 245-253, (2007).
Offenbacher et al., Maternal Periodontitis and Prematurity, Part I: Obstetric Outcome of Prematurity and Growth Restriction, Annual Periodontology, vol. 6, pp. 164-174, (2001).
Offenbacher et al., "Effects of Maternal Campylobacter Rectus Infection on Murine Placenta, Fetal and Neonatal Survival, and Brain Development," Journal of Periodontology, vol. 76, pp. 2133-2143, (2005).
Ogaard et al., "Professional Topical Fluoride Applications—Clinical Efficacy and Mechanism of Action," Advances in Dental Research, vol. 8(2), pp. 190-201, (1994).
oxyfresh.com, "Fluoride with Fresh Mint Mouthrinse," Oral Health Care, Oxyfresh Worldwide, Inc., http://web.archive.org/web/20061023030535/https://oxyfresh.com/dental/rinse_flouride.asp., 2 pages, (2006).
oxyfresh.com, "Fluoride with Fresh Mint Mouthrinse," Oral Health Care, Oxyfresh Worldwide, Inc., http://web.archive.org/web/20080509170508/https://oxyfresh.com/dental/rinse_flouride.asp., 2 pages, (2008).
oxyfresh.com, "Fluoride Kit," Oral Health Care, Oxyfresh Worldwide, Inc., http://web.archive.org/web/20061023030354/https://oxyfresh.com/dental//ohkits_flouride . . . , 2 pages, (2007).
Padilla et al., "Periodontal Pathogens in Atheromatous Plaques Isolated from Patients with Chronic Periodontitis," Journal of Periodontal Research, vol. 41, pp. 350-353, (2006).
Pappas, et al., "A Prospective Observational Study of Candidemia: Epidemiology, Therapy, and Influences on Mortality in Hospitalized Adult and Pediatric Patients," Clinical Infectious Diseases, vol. 37, pp. 634-643, (2003).
Pashley, "Dynamics of the Pulpo-Dentin Complex," Critical Reviews in Oral Biology & Medicine, vol. 7, pp. 104-133, (1996).
Penn-Barwell et al., "Comparison of the Antimicrobial Effect of Chlorhexidine and Saline for Irrigating a Contaminated Open Fracture Model," Journal of Orthopaedic Trauma, (2012).
Pfaller, et al., "Epidemiology of Invasive Candidiasis: A Persistent Public Health Problem," Clinical Microbiology Reviews, vol. 20(1), pp. 133-163, (2007).
Pushalkar et al., "Oral Microbiota and Host Innate Immune Response in Bisphosphonate-Related Osteonecrosis of the Jaw," International Journal of Oral Science, vol. 6, pp. 219-226, (2014).
Rautemaa et al., "Oral Infections and Systemic Disease—An Emerging Problem in Medicine," Clinical Microbiology and Infection, vol. 13(11), pp. 1041-1047, (2007).
Redding et al., "*Candida glabrata* is an Emerging Cause of Oropharyngeal Candidiasis in Patients Receiving Radiation for

(56) References Cited

OTHER PUBLICATIONS

Head and Neck Cancer," Oral Surgery, Oral Medicine, Oral Pathology, Oral Radiology, and Endodontics, vol. 97, pp. 47-52, (2004).
Redding, "The Role of Yeasts Other Than *Candida albicans* in Oropharyngeal Candidiasis," Current Opinion in Infectious Diseases, vol. 14, pp. 673-677, (2001).
Rees et al., "The Epidemiological Features of Invasive Mycotic Infections in the San Francisco Bay Area, 1992-1993: Results of Population-Based Laboratory Active Surveillance," Clinical Infectious Diseases, vol. 27, pp. 1138-1147, (1998).
Rex et al., "Development of Interpretive Breakpoints for Antifungal Susceptibility Testing: Conceptual Framework and Analysis of In Vitro-In Vivo Correlation Data for Fluconazole, Itraconazole, and Candida Infections," Clinical Infectious Diseases, vol. 24(2), pp. 235-247, (1997).
Rex et al., "Practice Guidelines for the Treatment of Candidiasis," Clinical Infectious Diseases, vol. 30(4), pp. 662-278, (2000).
Robinson et al., "The Chemistry of Enamel Caries," Critical Reviews in Oral Biology & Medicine, vol. 11(4), pp. 481-495, (2000).
Roller et al., "Mode of Bacterial Inactivation by Chlorine Dioxide," Water Research, vol. 14, pp. 635-641, (1980).
Rose et al., "Periodontics: Medicine, Surgery, and Implants," St. Louis: Mosby, Inc., pp. 20, 70, 847-848 and 854, (2004).
Rosella et al., "Medication-Related Osteonecrosis of the Jaw: Clinical and Practical Guidelines," Journal of International Society of Preventive & Community Dentistry, vol. 6(2), pp. 97-104, (2016).
Ruggiero et al., "Osteonecrosis of the Jaws and Bisphosphonate Therapy," Journal of Dental Research, vol. 86(11), pp. 1013-1021, (2007).
Samaranayake et al., "Oral Candidiasis and Human Immunodeficiency Virus Infection," Journal of Oral Pathology and Medicine, vol. 18, pp. 554-564, (1989).
Samonis et al., "Oropharyngeal Candidiasis as a Marker for Esophageal Candidiasis in Patients with Cancer," Clinical Infection Diseases, vol. 27, pp. 283-286, (1998).
San-Blas et al., "Fungal Morphogensis and Virulence," Medical Mycology, vol. 38(1), pp. 79-86, (2000).
Sedghizadeh et al., "Identification of Microbial Biofilms in Osteonecrosis of the Jaws Secondary to Bisphosphonate Therapy," Journal of Oral Maxillofacial Surgery, vol. 66(4), pp. 767-775, (2008).
Sharon et al., "The Effect of Chlorhexidine Mouth Rinses on Oral Candida in a Group Leukemic Patients," Oral Surgery, Oral Medicine, and Oral Pathology, vol. 44(2), pp. 201-205, (1977).
Sharma et al., "Oral Manifestations in HIV/AIDS Infected Patients from India," Oral Diseases, vol. 12, pp. 537-542, (2006).
Shemesh et al., "The Biocide Chlorine Dioxide Stimulates Biofilm Formation in *Bacillus subtilis* by Activation of the Histidine Kinase KinC," Journal of Bacteriology, vol. 192(24), pp. 6352-6356, (2010).
Shinada et al., "A Randomized Double Blind Crossover Placebo-Controlled Clinical Trial to Assess the Effects of a Mouthwash Containing Chlorine Dioxide on Oral Malodor," Trials, vol. 9(1), 8 Pages, (2008).
Shinada et al., "Effects of a Mouthwash with Chlorine Dioxide on Oral Malodor and Salivary Bacteria: A Randomized Placebo-Controlled 7-Day Trial," Trials, vol. 11(14), 11 Pages, (2010).
Silwood et al., A Multifactorial Investigation of the Ability of Oral Health Care Products (OHCPs) to Alleviate Oral Malodour, Journal of Clinical Periodontology, vol. 28, pp. 634-641, (2001).
Slavinsky et al., "Th1/Th2 Cytokine Profiles in Saliva of HIV-Positive Smokers with Oropharyngeal Candidiasis," Oral Microbiology and Immunology, vol. 17, pp. 38-43, (2002).
Socransky et al., "Microbial Complexes in Subgingival Plaque," Journal of Clinical Periodontology, vol. 25, pp. 134-144, (1998).
Soolari et al., "Phosphate Buffer-Stabilized 0.1% Chlorine Dioxide-Containing Mouth Wash Facilitated Sequestration of Bisphosphonate Related Osteonecrosis of the Jaw (BRONJ) Lesion From a Patient Who Presented with Osteonecrosis of the Jaw and a History of Intravenous Bisphosphonate Use: A Case Report," Translational Biomedicine, vol. 1(7), (2010).

Soolari et al., "Closure of an Open Wound Associated with Bisphosphonate-Related Osteonecrosis of the Jaw in a Breast Cancer Patient," Open Dentistry Journal, vol. 5, 5 Pgs., (2011).
Soysa et al., "The Impact of Cigarette/Tobacco Smoking on Oral Candidiasis: An Overview," Oral Diseases, vol. 11, pp. 268-273, (2005).
Speight, Lange's Handbook of Chemistry, 16th Edition, New York, McGraw-Hill, Section 1, pp. 301-302, (2005).
Spellberg et al., "Current Treatment Strategies for Disseminated Candidiasis," Clinical Infection Diseases, vol. 42, pp. 244-251, (2006).
Stookey et al., "Animal Caries Models for Evaluating Fluoride Dentifrices," Advances in Dental Research, vol. 9(3), pp. 198-207, (1995).
Takasawa et al., "An Elderly Case of Type 2 Diabetes Which Developed in Association with Oral and Esophageal Candidiasis," Internal Medicine, vol. 46(7), pp. 387-390, (2007).
Taylor et al., "Special Review in Periodontal Medicine, Periodontal Disease: Associations with Diabetes, Glycemic Control and Complications," Oral Diseases, vol. 14, pp. 191-203, (2008).
The Proprietary Association Subgroup on Fluoride Dentifrices, "Standards for Fluoride Dentifrices," 4 Pgs., (1978).
Thompson et al., "Coevolution of Morphology and Virulence in *Candida* Species," Eukaryotic Cell, vol. 10(9), pp. 1173-1182, (2011).
United States Environmental Protection Agency, "Alternative Disinfectants and Oxidants Guidance Manual," 2 Pgs., (1999).
US Code of Federal Regulations, Title 21: "Food and Drugs, Section 101.9 Nutrition Labeling of Food," 25 Pages, (2011).
Vargas et al., "Carriage Frequency, Intensity of Carriage, and Strains of Oral Yeast Species Vary in the Progression to Oral Candidiasis in Human Immunodeficiency Virus-Positive Individuals," Journal of Clinical Microbiology, vol. 40(2), pp. 341-350, (2002).
Vazquez, "Diagnosing and Managing Oropharyngeal Candidiasis," Infections in Medicine, vol. 24, pp. 427-436, (2007).
Viale, "Candida Colonization and Candiduria in Critically Ill Patients in the Intensive Care Unit," Drugs, vol. 69(1), pp. 51-57, (2009). (Abstract Only).
Villhauer et al., "Bactericidal Activity of Stabilized Chlorine Dioxide Against Polymicrobial Biofilms," International Assoc. for Dental Research Poster #3417, General Session, 1 page, (2009). (Abstract Only).
Villhauer et al., "Bactericidal Activity of Stabilized Chlorine Dioxide Rinse," American Association for Dental Research Meeting and Exhibition, 1 Page, (2008). (Abstract Only).
Wang et al., "Mimicking the Self-Organized Micro structure of Tooth Enamel," The Journal of Physical Chemistry C Nanomaterials and Interfaces, vol. 112(15), pp. 5892-5899, (2008).
Warrick et al., "Caries-Preventive Effects of Sodium and Amine Fluoride Dentifrices," American Journal of Dentistry, vol. 12(1), pp. 9-13, (1999).
Wei et al., "Plasma Membrane Damage to *Candida albicans* Caused by Chlorine Dioxide (ClO2)," Letters in Applied Microbiology, vol. 47(2), pp. 67-73, (2008).
Werner et al., "Are Alcohol Containing Mouthwashes Safe?" British Dental Journal, vol. 207(10), E19, pp. 488-489, (2009).
Whelton et al., ""The Use of Combinations of Caries Preventive Procedures,"" Journal of Dental Education, vol. 65(10), pp. 1110-1113, (2001).
Whitten et al., General Chemistry (6th Ed) Fort Worth, TX, Keeney-Kennicutt & Tang, ISBN 978-0-03-072373-5, pp. 27-46, (2000).
Williams et al., "Isolation and Identification of Candida From the Oral Cavity," Oral Diseases, vol. 6(1), pp. 3-11, (2000).
Willis et al., "Oral Candidal Carriage and Infection in Insulin-Treated Diabetic Patients," Diabetic Medicine, vol. 16, pp. 675-679, (1999).
Wirthlin et al., "Chlorine Dioxide and Water Rinses in Gingivitis," Rowpar Pharmaceuticals Study Report, OSAP Annual Symposium, (2003). (Abstract Only).
Wirthlin et al., "Formation and Decontamination of Biofilms in Dental Unit Waterlines," Journal of Periodontology, vol. 74(11), pp. 1595-1609, (2001).

(56) References Cited

OTHER PUBLICATIONS

Wirthlin et al., "Effects of Stabilized Chlorine Dioxide and Chlorhexidine Mouthrinses In Vitro on Cells Involved in Periodontal Healing," Journal of Western Society of Periodontology Abstracts, vol. 54(3), pp. 67-71, (2006).

Worihington et al.,. "Interventions for Treating Oral Candidiasis for Patients with Cancer Receiving Treatment (Review)," Cochrane Database of Systemic Reviews, Issue 2, 6 Pages, (2007).

Yilmaz et al., "Intercellular Spreading of *Porphyromonas gingivalis* Infection in Primary Gingival Epithelial Cells," Infection and Immunity, vol. 74(1), pp. 703-710, (2006).

Yu et al., "Caries Inhibition Efficacy of an Antiplaque/Antigingivitis Dentifrice," American Journal of Dentistry, vol. 14, pp. 14C-17C, (2000).

Zero, "Dentifrices, Mouthwashes, and Remineralization/Caries Arrestment Strategies," BMC Oral Health, vol. 6(S9), 13 Pages, (2006).

Non-Final Office Action dated Dec. 21, 2018 in U.S. Appl. No. 13/131,506.

PCT; International Search Report dated Nov. 30, 2018 in International Application No. PCT/US2018/049302.

PCT; Written Opinion dated Nov. 30, 2018 in International Application No. PCT/US2018/049302.

Brennan, "Examples of Acidic Buffers," Examples of Acid Buffering, Sciencing, https://sciencing.com/examples-acidic-buffers-6926552.htm, 3 Pages, (Apr. 25, 2018).

USPTO; Final Office Action dated Feb. 28, 2019 in U.S. Appl. No. 15/605,506.

USPTO; Non-Final Office Action dated Mar. 8, 2019 in U.S. Appl. No. 11/774,730.

EPO; Extended European Search Report dated Jan. 20, 2020 for European Application No. 18785801.4; 9 pp.

Russian Office Action and Search Report dated Mar. 30, 2022 in corresponding Russian Patent Application No. 2019114126 filed Sep. 3, 2018; total 13 pages.

\* cited by examiner

ALIPHATIC ANIONIC COMPOUNDS AND OXIDATIVE COMPOUNDS WITH IMPROVED STABILITY AND EFFICACY FOR USE IN PHARMACEUTICAL COMPOSITIONS

CROSS-REFERENCE TO RELATED APPLICATIONS

This application claims priority to, and the benefit of: PCT Application No. PCT/US2018/049302, filed on Sep. 3, 2018, entitled "ALIPHATIC ANIONIC COMPOUNDS WITH IMPROVED STABILITY AND EFFICACY FOR USE IN PHARMACEUTICAL COMPOSITIONS"; U.S. Provisional Patent Application No. 62/676,170 filed on May 24, 2018 entitled "ALIPHATIC ANIONIC COMPOUNDS AND OXIDATIVE COMPOUNDS WITH IMPROVED STABILITY AND EFFICACY FOR USE IN PHARMACEUTICAL COMPOSITIONS"; U.S. Provisional Patent Application No. 62/553,450 filed on Sep. 1, 2017 entitled "ALIPHATIC ANIONIC COMPOUNDS AND OXIDATIVE COMPOUNDS WITH IMPROVED STABILITY AND EFFICACY FOR USE IN PHARMACEUTICAL COMPOSITIONS". The contents of each of the foregoing applications are hereby incorporated by reference for all purposes (except for any subject matter disclaimers or disavowals, and except to the extent that the incorporated material is inconsistent with the express disclosure herein, in which case the language in this disclosure controls).

TECHNICAL FIELD

The present disclosure relates generally to a multi-component composition comprising a combination of an aliphatic anionic compound and an oxidative compound.

BACKGROUND

Oxidative compounds interact with various cellular components, causing, for example, peroxidation and disruption of membrane layers, oxidation of oxygen scavengers and thiol groups, enzyme inhibition, oxidation of nucleosides, impaired energy production, and/or disruption of protein synthesis and, possibly, cell death. Biomolecules produced by cells and various other chemical compounds also may be oxidized by the oxidative compounds.

Different compounds tend to interact with cellular components differently, producing differing biological results. For example, hydrogen peroxide may be more effective in controlling *Pseudomonas aeruginosa* and *Stenotrophomonas maltophilia* than peracetic acid (PAA). Similarly PAA may be more effective than chlorine dioxide ($ClO_2$) at preventing growth of *Escherichia coli, Listeria monocytogenes*, and *Salmonella typhimurium*. The biocidal activity of one oxidative compound or composition cannot readily predict the biocidal activity of another oxidative compound or composition.

Nonetheless, it may be desirable to add certain oxidative compounds to certain drug products and other therapeutic preparations, including prescription and over-the-counter products and preparations, including cosmetic preparations. Formulating and manufacturing such a product or preparation can be difficult however because of the reactivity of such oxidizing compounds, particularly at the required pH range and selecting other ingredients for such products or preparations. Among others, oxidative compounds may react chemically, such as with the hydroxy groups of alcohols and polyhydroxy compounds. For example, chlorine dioxide in aqueous solution with the desired pH range from about 6.0 to about 8.0 decomposes to the chlorite and chlorate ions. Sodium chlorite is a common source of chlorine dioxide. This may lead to degradation of the oxidative compounds, the active ingredient(s), or other excipients in a multi-component composition. Such degradation may reduce the efficacy or needed shelf-life of the intended product. Accordingly, various challenges confront the manufacture of pharmaceutical and cosmetic products containing oxidative compounds. Thus, the achievement and maintenance of the stability of oxidizing compounds is an important and desired characteristic for commercial uses and applications.

One such product may be a fluoride toothpaste composition. Here, it may be desirable to maintain and extend the stability of the active ingredient(s) (e.g., fluoride ion), and other excipients, such as flavor, including stabilized chlorine dioxide or sodium chlorite. Stability may be considered from the time of manufacture, through distribution and sale, to the time of intended use.

The U.S. Pharmacopoeia (USP) defines the stability of a pharmaceutical product as "extent to which a product retains within specified limits and throughout its period of storage and use, i.e., its shelf life, the same properties and characteristics that it possessed at the time of its manufacture." http://www.pharmacopeia.cn/v29240/usp29nf24s0_c1191.html (last visited September 2018).

SUMMARY OF THE INVENTION

In accordance with various aspects, a multi-component composition is provided, as well as various formulations of the multi-component composition, including methods of administration and methods of use. In one aspect, the multi-component composition comprises an aliphatic anionic compound and an oxidative compound. In embodiments, the multi-component composition may comprise N-acyl sarcosinate and stabilized chlorine dioxide.

In embodiments, multi-component composition is provided, comprising: from about 0.01% to about 5.0% of an aliphatic anionic compound, based on a total weight of the multi-component composition; from about 0.001 to about 8% of an oxidative compound, based on a total weight of the multi-component composition; a buffering system, wherein pH of the multi-component composition is between 6.0 and 8.0; and water. In further embodiments, the aliphatic anionic compound facilitates stability of the oxidative compound. In further embodiments, the aliphatic compound facilitates efficacy of the composition.

In further embodiments, the aliphatic anionic compound comprises, at least one of, N-acyl sarcosinate, taurates, sodium lauryl sulfoacetate, sodium lauryl isethionate, sodium laureth carboxylate.

In further embodiments, the N-acyl sarcosinate is, at least one of, sodium lauroyl sarcosinate, sodium cocoyl sarcosinate, sodium myristoyl sarcosinate, sodium oleoyl sarcosinate, or sodium stearoyl sarcosinate.

In further embodiments, the oxidative compound comprises, at least one of, ammonium peroxydisulfate, carbamide (urea) peroxide, ferric chloride, hydrogen peroxide, potassium bromate, potassium chlorate, potassium perchlorate, potassium dichromate, potassium ferricyanide, potassium peroxymonosulfate, potassium persulfate, sodium bromate, sodium chlorate, sodium perchlorate, sodium chlorite, sodium hypochlorite, sodium iodate, sodium perborate, sodium percarbonate, sodium persulfate, stabilized chlorine dioxide, strontium peroxide, and zinc peroxide.

In certain aspects, the multi-component composition is formulated in at least one of a mouth rinse, a gum, a gel, a paste, a cream, and a lozenge.

In various embodiments, the multi-component composition comprises an orally acceptable aqueous vehicle comprising, at least one, a humectant, an abrasive, a pharmaceutically acceptable carrier, a fluoride ion source, and a thickening agent.

In further embodiments, the multi-component composition oxidizes salivary biomolecules.

In further embodiments, the multi-component composition oxidizes salivary biomolecules in 30 to 120 seconds of contact with saliva.

In some embodiments, the salivary biomolecules are pyruvate and L-methionine.

In further embodiments, the multi-component composition is applied to, at least one of, anal, aural, nasal, oral, and urogenital cavities.

In further embodiments, less than 20% of the oxidative compound is destabilized after 3 months at 40±1° C. and 70-75% relative humidity or one year under ambient conditions.

In further embodiments, the oxidative compound is stabilized chlorine dioxide, wherein less than 20% of the stabilized chlorine dioxide is degraded after 3 months at 40±1° C. and 70-75% relative humidity or one year under ambient conditions.

In certain aspects, an oral care composition is provided, comprising: from about 0.01% to about 5.0% of an N-acyl sarcosinate, based on a total weight of the oral care composition; from about 0.001 to about 8% of an oxidative compound, based on the total weight of the oral care composition; a buffering system, wherein pH of the multi-component composition is between 6.0 and 8.0; and water, wherein the N-acyl sarcosinate provides enhanced stability and efficacy for the oxidative compound in the oral care composition.

In further embodiments, the oral care composition further comprises, at least one of, a humectant, a whitening agent, a thickening agent, a fluoride ion source, a sweetening agent, an abrasive, a flavoring agent, a coloring agent, and a gelling agent.

In further embodiments, the oral care composition is a dentifrice.

In further embodiments, less than 20% of the oxidative compound is degraded in 3 months at 40±1° C. and 70-75% relative humidity or one year under ambient conditions.

In some embodiments, the buffering system comprises disodium hydrogen phosphate and sodium dihydrogen phosphate.

In further embodiments, the oral care composition decreases regrowth of an oral polymicrobial biofilm.

In further embodiments, the oral care composition effectively reduces regrowth of the oral polymicrobial biofilm in 24 hours.

In further embodiments, the oral care composition enhances remineralization of tooth enamel.

In further embodiments, the oral care composition oxidizes salivary biomolecules such as pyruvate and L-methionine in 30 to 60 seconds of contact with the saliva in the oral cavity.

In further embodiments, the oral care composition provides an increased amount of available chlorite ion.

In some aspects, a method for enhancing fluoride uptake into an oral cavity is provided, comprising: preparing an oral care composition comprising from about 0.01% to about 5.0% of an N-acyl sarcosinate, based on a total weight of the oral care composition, from about 0.001 to about 8% of an oxidative compound, based on the total weight of the oral care composition, a buffering system, wherein pH of the multi-component composition is between 6.0 and 8.0, water; and applying the oral care composition to the oral cavity.

In further embodiments, the enhanced fluoride uptake into the oral cavity is increased by at least 2-fold.

In further embodiments, the enhanced fluoride uptake into the oral cavity is increased by at least 4-fold.

In further embodiments, the oral care composition enhances fluoride uptake.

In certain aspects, a method to decrease regrowth of oral polymicrobial biofilm is provided, comprising: preparing an oral care composition comprising from about 0.01% to about 5.0% of an N-acyl sarcosinate, based on a total weight of the oral care composition, from about 0.001 to about 8% of an oxidative compound, based on the total weight of the oral care composition, a buffering system, wherein pH of the multi-component composition is between 6.0 and 8.0, water; and applying the oral care composition to an oral cavity.

In further embodiments, the oral care composition decreases regrowth of oral polymicrobial biofilm.

The contents of this section are intended as a simplified introduction to the disclosure, and are not intended to limit the scope of any claim.

BRIEF DESCRIPTION OF THE DRAWING FIGURES

DETAILED DESCRIPTION

Definitions

Figure 1:
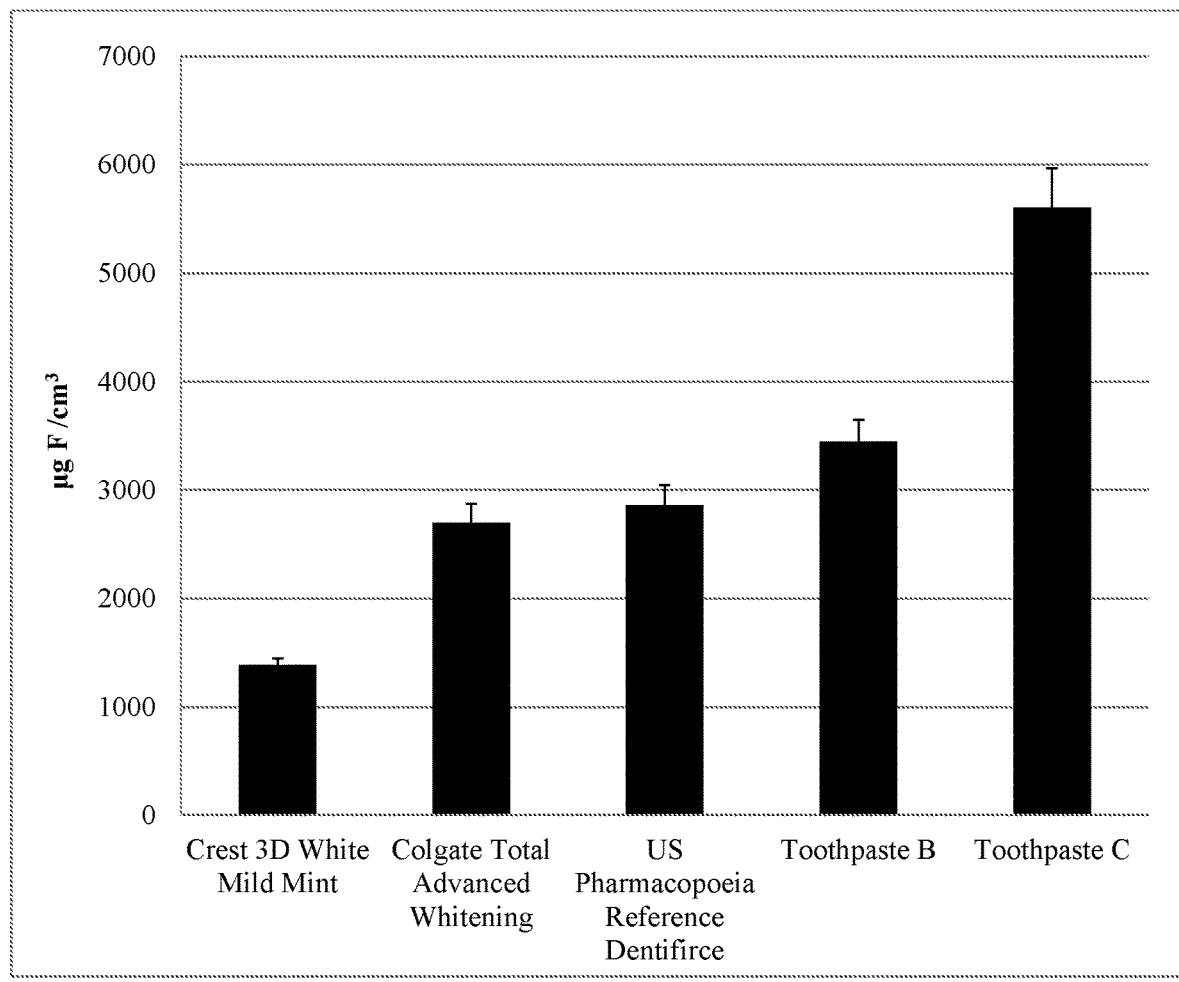
FIG. 1 is a graph illustrating fluoride uptake of commercial products and an oral care composition according to an embodiment.

The following is a list of definitions for terms used herein. Unless defined otherwise, all technical and scientific terms used herein generally have the same meaning as commonly understood by one of ordinary skill in the art. In the event that there is a plurality of definitions for a term herein, those in this section prevail unless stated otherwise. Generally, the nomenclature used herein and the laboratory procedures in cytopathicity analysis, microbial analysis, organic, physical and inorganic chemistry, and dental clinical research are those well-known and commonly employed in the art.

As used herein, "about" will be understood by persons of ordinary skill in the art and will vary to some extent on the context in which it can be used. Generally, "about" encompasses a range of values that are plus/minus 10% of a reference value, unless specifically defined. For instance, "about 25%" encompasses values from 22.5% to 27.5%.

As used herein, "acid source" means a biological material, usually a particulate material, or which is itself acidic or produces an acidic environment when in contact with liquid water or oxychlorine anion.

As used herein, "ambient conditions" means approximately room temperature (e.g., 20-35° C.) and relative humidity of approximately <70%.

As used herein, "a reasonable period of time" means the time, ranging from months to years, depending upon the application, a composition may be expected to maintain a safe and efficacious amount of its combined ingredients.

As used herein, "shelf-life stable" and "shelf-life stability" are used interchangeably and refer to the multi-component composition being deemed consumer acceptable after a defined period of time after its production (under ambient conditions).

As used herein, "bioavailability" means to the absorption or penetration of the active agent(s) of the composition into the organic matter to which it is exposed and/or the absorption rate proportion of the dose of the composition that reaches the systemic circulation of the organic matter for which its use is intend. For example, when a composition is administered intravenously, its bioavailability is nearly 100%, while when the composition is administered topically, a fraction of the total composition reaches systemic circulation. Some embodiments described herein provide enhanced penetration or absorption of oxidative compounds when applied topically to organic matter. The term "bioavailability" also refers to its availability for efficacy at the desired site and for efficacy that either intracellular, extracellular or within biofluids/biological fluids.

As used herein, "aliphatic anionic compounds" means aliphatic compounds comprising anionic moiety that exhibit surface active properties, ionic interactions with other compounds, physical interaction, etc. as a result of combined physico-chemical properties of aliphatic and anionic structural moieties.

As used herein, "oxidative compounds" means compounds exhibiting oxidation reaction of biomolecules such as organic acids, amino acids, sulfur compounds, precursors of sulfur compounds, proteins, enzymes etc.

As used herein, "biocidal", "bactericidal", "fungicidal" or synonymous terms means the property of inactivating or killing microorganisms, such as bacteria, algae, yeast, and fungi. As used herein, "biocidal" also refers to the effect of a composition as a treatment for reduction of bacterial or fungal or microbial growth or overgrowth in fluids or biofilm which may be associated with alleviating a diseased condition or state.

As used herein, "biostatic", "bacteriostatic", "fungistatic" or synonymous terms means the property of arresting the growth of microorganisms, such as bacteria, algae, yeast and fungi. As used herein, "biostatic" means to the effect of a composition in maintaining the polymicrobial mixture of a fluid or a biofilm, as in maintaining the oral ecology so that one or more organisms have not overgrown to enable inflection and disease. Compositions with biostatic attributes are useful in health maintenance, wellness and prevention of infection and disease.

As used herein, "stabilized chlorine dioxide," means an aqueous solution comprised of sodium chlorite or chlorite ion source and a compounds or compounds intended to inhibit or slow the degradation of the chlorite or chlorite ion source.

As used herein, a "biofilm" means a biological aggregate that forms a layer on a surface, the aggregate comprising a community of microorganisms embedded in an extracellular matrix of polymers and/or other biocompounds such as glycoproteins. Typically, a biofilm comprises a diverse community of microorganisms, including bacteria (aerobic and anaerobic), algae, protozoa, yeast, and fungi. While mono-species biofilms also exist, biofilms in vivo become polymicrobial as they develop overtime creating oxygen-scare environments where anaerobic pathogens thrive and where the biofilm matrix protects the polymicrobial mixture within from antimicrobial treatment.

As used herein, "buffering system" means a system containing two or more agents characterized as an acid and its conjugate base or vice versa. Suitable components of buffering system may include carbonates, borates, phosphates, imidazole, citrates, acetates and mixtures thereof, and further may include any of monosodium phosphate, disodium phosphate, trisodium phosphate, alkali metal carbonate salts, imidazole, pyrophosphate salts, acetic acid, sodium acetate, citric acid, and sodium citrate. Exemplary compounds used in generating buffering system are described in more detail in Kirk & Othmer, Encyclopedia of Chemical Technology, Fourth Edition, Volume 18, Wiley-Interscience Publishers (1996).

As used herein, "pH modifying agent" means an agent capable of modifying pH. pH modifying agents include acidifying agents to lower pH, basifying agents to raise pH and buffering agents to control pH within a desired range. Use or presence of single pH modifying agent may not result in a buffered composition.

As used herein "a carrier" means those components of a composition that are capable of being commingled to provide required physical consistency and consumer goodness properties without interaction with other ingredients.

As used herein, "orally acceptable carrier" means a suitable vehicle or ingredient, which can be used to form and/or apply the present compositions to the oral cavity in a safe and effective manner.

As used herein, "compatible" means that the components of the composition are capable of being commingled without interaction in any manner which would substantially reduce the stability of the oxidative compounds, ingredients required for the efficacy, the carrier and excipients, and the consumer qualities of the composition.

As used herein, "consumer goodness qualities" include, but are not limited to, appearance, viscosity, taste, odor, abrasiveness, color, flavor, and moisturizing attributes of the compositions deemed desirable by consumers through consumer product testing or other such means. For example, it may be desirable that a tube of toothpaste produce a ribbon stripe of toothpaste on a toothbrush when squeezed and that the toothpaste composition is neither too firm to be squeezed easily from the tube nor too viscous so as not to hold or rest on the toothbrush ready or use.

As used herein, "dental plaque" means a polymicrobial biofilm that forms on the surface of teeth.

As used herein, "dual phase composition" means a composition wherein certain ingredients are contained in one part and other ingredients are contained separately in a second part at the time of manufacture and prior to use to prevent the reactivity of the oxidative compounds to the carrier and other excipients of the composition. The bioavailability of dual phase compositions may be determined once the two phases are mixed at the time of use. A difference between single phase and dual phase compositions may include how shelf-life is determined. Because the two phases of a dual phase compositions are combined just prior to usage, the shelf-life stability of dual phase compositions is the short period from the time of mixing just prior to use to the time of use which may occur immediately thereafter. Dual-phase compositions may not have the required attribute of maintaining stability of components from the time of manufacture to the time of usage precisely because the phases of the composition are not intended to be mixed until just prior to usage.

As used herein, "essentially free" means a composition which is comprised of very low levels, below detection levels of commonly used analytical methods, of a specific ingredient or compound or molecule.

As used herein, "vehicle" means an orally-acceptable dentifrice vehicle used to prepare a dentifrice composition comprising a water-phase, containing a humectant therein.

As used herein, "dentifrice" means paste, gel, powder, tablets, or liquid formulations, unless otherwise specified, that are used to clean the surfaces of the oral cavity.

As used herein, "teeth" refers to natural teeth as well as artificial teeth or dental prosthesis.

As used herein, "efficacious amount" means any amount of the agent that may result in a desired biocidal or biostatic or chemical or physiological effect, a desired cosmetic effect, and/or a desired therapeutic biological effect. In one example, an efficacious amount of an agent used for tooth whitening may be an amount that may result in whitening of a tooth with one or more treatments. In another example, an efficacious amount of an agent used for wound treatment is an amount that may result in a statistically significant improvement in wound healing.

As used herein, "film" means a layer of a material having two dimensions substantially larger than the third dimension. A film may be a liquid or a solid material. For some materials, a liquid film can be converted into a solid film by curing, for instance, by evaporation, heating, drying, cross-linking, adhering, adduct formation, and like phenomena.

As used herein, "hard tissue" means any toe and finger nail, hard keratinized tissue, hard tooth tissue, bone, tooth and the like, found in animals such as mammals.

As used herein, "irritating" and "irritation" refer to the property of causing a local inflammatory response, such as reddening, swelling, itching, burning, or blistering, by immediate, prolonged, or repeated contact. For example, inflammation of a non-oral mucosal or dermal tissue in a mammal can be an indication of irritation to that tissue. A composition may be deemed "substantially non-irritating" or "not substantially irritating," if the composition is judged to be slightly or not irritating using any standard method for assessing dermal or mucosal irritation.

As used herein, "pharmaceutically acceptable" is set forth broadly and refers without limitation to those compounds, materials, compositions and/or dosage forms which are, within the scope of sound medical judgment suitable for contact with the tissues of and/or for consumption by human beings and animals without excessive toxicity, irritation, allergic response, or other problem complications commensurate with a reasonable risk/benefit ratio.

As used herein, the abbreviation "ppm" means parts per million by weight or volume as applicable.

As used herein, "overgrowth" refers to excessive concentrations of bacteria, algae, yeast, and/or fungi leading to inflammation, infection, pathogenesis and disease. Overgrowth may occur in biofilms and plaques containing polymicrobial mixtures of bacteria, algae, yeast, and/or fungi, such as those found in the biofilms associated with mucositis and with dental plaque. Overgrowths of pathogenic microbes within biofilms are known to increase significantly their resistance to treatment and increase the incidence of inflamed tissues, infection and disease.

As used herein, "prophylactic" means treatment administered to a subject who does not exhibit signs of a disease or exhibits early signs of the disease for the purpose of decreasing the risk of developing pathology associated with the disease.

As used herein, "range" means the area of variation between upper and lower limits on a particular scale. It is understood that any and all whole or partial integers between any ranges set forth herein are included herein.

As used herein, "safe and effective amount" and similar terms mean an amount of an ingredient, such as the amount of an oxidative compound, in composition of sufficient dosage to positively modify the condition to be treated, but low enough to be safe for humans and animals to use without serious side effects (at a reasonable benefit/risk ratio), within the scope of sound medical/dental judgment. "Safe and effective" pertains not only to the dosage amount but also the dosage rate (rate of release) of the oxidative compound applied in treatment. The safe and effective amount of oxidative compound in a composition may vary with the particular condition being treated, the age and physical condition of the patient being treated, the severity of the condition, the duration of treatment, the nature of concurrent therapy, the specific form (e.g., salt) of the oxidative compound employed, and the particular vehicle from which the oxidative compound is applied.

As used herein, a "single phase composition" means a composition wherein all ingredients are composed in a single container at the time of composing and are not mixed with other ingredients subsequently. Thus, single phase compositions are ready for use at any time during their shelf-life without further preparation or mixing. The bioavailability of single phase compositions may be determined at any point during their useful shelf-life.

As used herein, "stability" means the prevention of a reaction, reduction or degradation of components, such as of oxidative compounds, comprised in a multi-component composition. A multi-component composition may be "stable" if the oxidative compounds of the multi-component composition are not reactive with each other for a reasonable period of time. For example, a multi-component composition may stable if it maintains consumer qualities and exhibits less than 35% loss of the oxidative compounds for a period of 24 months at about 25° C. (ambient temperature) or 6 months at an accelerated temperature of 40°±2° C. and 75%±5% Relative Humidity (RH).

As used herein, "shelf-life" means the length of time compositions maintain the desired stability of the oxidative compounds and the consumer qualities of the composition. For example, a target or stable shelf life for a composition may not comprise more than 35% loss in the concentration of oxidative compound in 6 months at 40±2° C. and 75%±5% RH, which is equivalent to 2 years of shelf life at room temperature.

As used herein, "therapeutic" means intended to be administered to a subject who exhibits signs of pathology for the purpose of diminishing or eliminating those signs.

As used herein, "topical composition" means a product which is not intentionally ingested or otherwise applied without recovery for purposes of systemic administration of therapeutic agents, but is retained in the anal, aural, oral, nasal, ocular, or urogenital cavities or upon the skin or other outer surfaces of the body, or upon an area of affected soft tissue for a time sufficient to contact substantially all of the surfaces and/or tissues for purposes of administration and delivery of therapeutic agents.

As used herein, "wound" means a laceration, abrasion, puncture, burn, and/or other injury to any one or more soft and/or hard tissue. Exemplary tissues considered for such wound treatment include mucosal tissue and dermal tissue including epidermal tissue, dermal tissue, and subcutaneous tissue (also called hypodermis tissue). As used herein, a wound also encompasses a laceration, a puncture, and/or an avulsion of a fingernail or toenail. A wound can penetrate the tissue partially or completely. A wound can arise accidently or intentionally, e.g., a surgical wound.

As used herein, "dispersing agent" means a compound that improves the separation of particles and prevents settling or clumping of an ingredient(s) in a multicomponent composition.

As used herein, "emollient agent" means a compound that reduces the loss of water from a composition.

As used herein, "suspending or emulsifying agent" means a compound that achieves uniform dispersion of an ingredient(s) in a multicomponent composition.

As used herein, "fragrance" means a compound that provides a pleasing scent or order similar to perfume to a composition.

As used herein, "cooling agent" means a compound that provides a cooling, soothing, or pleasant feeling when a composition is topically applied to hard and soft tissues.

As used herein, "warming agent" means a compound that provide an olfactory sensation, especially warm sensation. Warming agents are often desired in various cosmetic preparations, such as shaving creams, hand lotions, body lotions, facial preparations, including masks, depilatories.

As used herein, "humectant" means a compound that preserves moisture in a composition. Some embodiments described herein include one or more compounds such as cellulose gum, carboxymethylcellulose, pectin, guar gum, xanthan gum, N-acyl sarcosinate, sodium lauroyl sarcosinate, sodium cocoyl sarcosinate, or sodium myristoyl sarcosinate.

As used herein, "thickener" means a compound that increases viscosity of a composition.

As used herein, "excipient" means a compound that provides physical and consumer goodness properties to a composition for its acceptance. Examples of such properties (but not limited to) are viscosity, appearance, flavor, color, thickness, sweetness, gel like structure, preservative, uniform suspension or combinations thereof.

As used herein, the term "abrasive agent" means a compound that helps to remove coating (or deposits) from hard or soft tissues, such as that on a tooth surface while brushing using a composition, such as a toothpaste.

As used herein, "desensitizing agent" means a compound that helps reduce or alleviate sensitivity and pain. For example, a desensitizing agent in a topical resin, varnish, toothpaste or mouthwash may occlude dentin tubules or may desensitize nerve fibers, blocking the neural transmission.

All percentages and ratios used herein are by weight of a multi-component composition and not of the overall topical formulation that is delivered, unless otherwise specified. All measurements are made at room temperature i.e. 20-25° C., unless otherwise specified. The concentration of a dissolved oxidative compound may depend on the temperatures and the range of humidity to which the solution is likely to be subjected. Heat and humidity, under normal circumstances, may cause such a composition to degrade from liquid to gas, changing its weight and rendering common assay calculations inaccurate.

Detailed Description of the Embodiments

In aspects, the multi-component composition comprises an oxidative compound. In embodiments, an oxidizing compound comprises at least one of a low-molecular-weight compound, a compound of suitable size and properties to permit diffusion or uptake through cell wall to react with internal cell components, and a compound which stimulates apoptotic or necrotic cell death. In further embodiments, the oxidizing compound includes compounds having a low oxidizing threshold, indicating that the selected oxidizing compounds interact strongly with its target by chemical rather than physical means. In further embodiments, the oxidative compound comprises, at least one of, chlorine dioxide or a chlorite ion source, such as stabilized chlorine dioxide, a chlorite salt, ammonium peroxydisulfate, carbamide (urea) peroxide, ferric chloride, hydrogen peroxide, potassium bromate, potassium chlorate, potassium perchlorate, potassium dichromate, potassium ferricyanide, potassium peroxymonosulfate, potassium persulfate, sodium bromate, sodium chlorate, sodium perchlorate, sodium chlorite, sodium hypochlorite, sodium iodate, sodium perborate, sodium percarbonate, sodium persulfate, strontium peroxide, zinc acetate, zinc peroxide, zinc chloride or the like.

In further embodiments, a multi-component composition may comprise from about 0.005% to about 8.0% oxidative compound, such as a chlorite ion sources and/or stabilized chlorine dioxide. In further embodiments, the multi-component composition may include from about 0.005% to about 4.0% oxidative compound. In further embodiment, the multi-component composition may include from about 0.005% to about 3.0% oxidative compound.

In another embodiment, the multi-component composition includes from about 0.005% to about 2.0% oxidative compound.

In certain aspects, the multi-component composition comprises an aliphatic anionic compound. In some embodiments, the aliphatic anionic compound comprises water-soluble salts having from about 8 to 20 carbon atoms in an alkyl radical, such as taurates, sodium lauryl sulfoacetate, sodium lauryl isethionate, and sodium laureth carboxylate. In some embodiments, the aliphatic anionic compound comprises an N-acyl sarcosinate compound. N-acyl sarcosinates may comprise the following general structure:

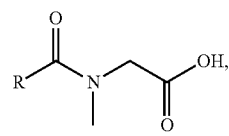

where R is typically a fatty acid of chain length $C_8$ to $C_{20}$. N-acyl sarcosinates may include lauroyl sarcosinate, cocoyl sarcosinate, myristoyl sarcosinate, oleoyl sarcosinate, stearoyl sarcosinate and other such compounds identifiable to a person skilled in the art. In embodiments, the aliphatic anionic compound are provided in the form of a salt or a pharmaceutically accepted salt, such as, sodium lauroyl sarcosinate, sodium lauryl sulfoacetate, sodium lauryl isethionate, sodium laureth carboxylate, sodium cocoyl sarcosinate, and sodium myristoyl sarcosinate.

In further embodiments, a multi-component composition is provided, comprising from about 0.001% to about 20.0% aliphatic anionic compound. In further embodiments, the multi-component composition includes from about 0.001% to about 10% of an aliphatic anionic compound. In further embodiments, the multi-component composition may include from about 0.001% to about 5.0% of an aliphatic anionic compound. In further embodiments, the multi-component composition includes from about 0.001% to 1% of an aliphatic anionic compound. In further embodiments, the multi-component composition includes from about 0.01% to 1% of an aliphatic anionic compound. In further embodiments, the multi-component composition includes from about 0.01% to 5% of an aliphatic anionic compound.

In further embodiments, the multi-component composition includes from about 0.2% to 5% of an aliphatic anionic compound. In further embodiments, the multi-component composition includes from about 0.5% to about 5% of an aliphatic anionic compound.

In certain aspects, the multi-component composition comprises a carrier. In embodiments, suitable carrier(s) comprise those that satisfy various considerations based on compatibility with the other ingredients required for the efficacy, consumer qualities, cost, and contribution to shelf stability. In embodiments, the selected carrier does not substantially reduce either the stability of the composition or its efficacy. Examples of suitable carriers variously include gelling agents, whitening agents, flavoring agents and flavoring systems, coloring agents, abrasive agents, foaming agents, desensitizing agents, dispersants, humectants, sweetening agents analgesic and anesthetic agents, anti-inflammatory agents, anti-malodor agents, anti-microbial agents, anti-plaque agents, anti-viral agents, biofilm disrupting, dissipating or inhibiting agents, cellular redox modifiers, antioxidants, cytokine receptor antagonists, dental anti-calculus agents, fluoride ion sources, hormones, metalloproteinase inhibitors, enzymes, immune-stimulatory agents, lipopolysaccharide complexing agents, tissue growth factors, vitamins and minerals, water, and mixtures thereof.

In aspects, the multi-component composition comprises a buffering system. The buffering system may be required to achieve and maintain a pH of the multi-component composition in the range required to prevent the degradation of the oxidative compound in the multi-component composition. In embodiments, the buffering system may comprise an acid and its conjugate base or a base and its conjugate acid. In embodiments, the buffering system may comprise an organic acid and its conjugate base or an organic base and its conjugate acid. In some embodiments, the buffering system may comprise an inorganic acid and its conjugate base or an inorganic base and its conjugate acid. In embodiments, the buffering system comprises an organic acid and an inorganic base or an inorganic acid and an organic base. In embodiments, the buffering system maintains a composition pH at a range from about 6.0 to about 8.5. A buffering system may also be useful to achieve consumer goodness properties. A buffering system generally differs from a single pH modifying agent used to reduce the pH of a composition or raise the pH of a composition.

In embodiments, a buffering system comprises from about 0.2% to about 4.0%, from about 0.05% to about 0.5%, from about 0.2% to about 2.0%, or from about 0.7% to about 4.2%, or from about 0.7% to about 2.2% of a base compound. In various embodiments, the buffering system comprises from about 0.01% to about 4.0%, from about 0.01% to about 0.10%, from about 0.01% to about 0.05%, from about 0.01% to about 0.05%, from about 0.04% to about 2.1% or from about 0.05% to about 2.2%, from about 0.06% to about 0.2%, from about 0.00% to about 0.1% of an acidic compound.

In aspects, the multi-component composition includes one or more pH modifying agents. pH modifying agents for use herein may include acidifying agents to lower pH, basifying agents to raise pH. For example, one or more compounds can provide a pH from about 2 to about 10, or from about 2 to about 8, or from about 3 to about 9, or from about 4 to about 8, or from about 5 to about 7, or from about 6 to about 10, or from about 6 to about 8, or from about 7 to about 8, or from about 7 to about 9, and any pH above or below this range or any fractional range in between. Orally acceptable pH modifying agent including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and mixtures thereof. One or more pH modifying agents are optionally present in a total amount effective to adjust the composition to an orally acceptable pH range.

In some embodiments, the multi-component composition may include from about 0.01% to about 10% pH modifier agents based on a total weight of the oral care composition. In some embodiments, the pH modifier agents may be from about 0.01%, 0.1%, 1%, 2%, 3%, 4%, 5%, 6%, 7%, 8%, 9% or to about 10% by weight or volume of the multi-component composition. In other embodiments, a pharmaceutically acceptable carrier may be in an amount from about 0.01% to about 5%, from about 0.01% to about 3%, or from about 0.01% to about 2%. Use or presence of single pH modifying agent generally does not result a buffered composition.

In some aspects, the multi-component composition may further comprise one or more additional active ingredients. In some embodiments, an additional active ingredient may include one or more of the following additional ingredients: fluoride ion sources, anti-microbial agents, analgesic compounds, anti-inflammatory agents, anti-malodor agents, anti-plaque agents, anti-viral agent, biofilm disrupting, dissipation or inhibiting agents, hormones, enzymes, metalloproteinase inhibitors, immune-stimulatory agents, and numbing agents. In further embodiments, the multi-component composition comprises one or more excipients including any of water, abrasives, humectants, thickeners, sweeteners, moisturizers, flavors, colors, fillers, and extenders.

In some aspects, the multi-component composition comprises a pharmaceutically acceptable carrier and/or excipients. Pharmaceutically-acceptable carriers include one or more compatible solid or liquid materials, including diluents or encapsulating substances, which are suitable for topical administration to the human or animal body and provide physical action or consumer-goodness characteristics acceptable to the user. The pharmaceutical carriers and/or excipients may be combined with the oxidative compounds in a single phase multi-component composition without interaction in any manner that would reduce the stability of the oxidative compound, the consumer goodness qualities, the safety and effectiveness of the composition in treating or preventing anal, aural, oral, nasal, ocular, urogenital, foot, and skin disorders, or diseases of the skin or foot and the inflammation and infection of tissues therein. The choice of a pharmaceutically acceptable carrier and/or excipient may be determined by the way the composition is to be introduced into the anal, aural, oral, nasal, ocular, or urogenital cavity, or to be applied topically in foot care and skin care. The pharmaceutically acceptable carrier and/or excipient may depend on secondary considerations such as, but not limited to, consumer goodness qualities, costs and shelf-life stability.

In embodiments, the pharmaceutically acceptable carrier and/or excipients may be in an amount of from about 0.01% to about 30%, for example, from about 0.01%, 0.1%, 1%, 2%, 3%, 4%, 5%, 6%, 7%, 8%, 9% or to about 10% by weight or volume of the multi-component composition. In other embodiments, the pharmaceutically acceptable carrier may be in an amount from about 0.01% to about 60%, from about 0.01% to about 30%, or from about 0.01% to about 20%.

In aspects, the multi-component composition further comprises an abrasive agent. Abrasives are useful as carriers of the multi-component compositions intended for specific oral and dermal applications and uses. For example, abrasive materials provide physical abrasion between toothbrush and teeth to clean pellicle, cuticle, biofilm, plaque, stain, and calculus, while also contributing to the structure of an embodiment and maintaining stability of the overall formulation. In certain dermal embodiments, it may be desirable for the composition to assist in the exfoliation of skin tissues. In some embodiments, the abrasive material is selected from a composition that does not excessively abrade skin, enamel, dentin, or other hard or soft tissues. In embodiments, the abrasive agent comprises, for example, silicas, hydrated silicas, including gels and precipitates; insoluble sodium polymetaphosphate; hydrated alumina; calcium carbonate; calcium hydrogen orthophosphate dihydrate (known in the trade as "dicalcium phosphate"); tricalcium phosphate, calcium polymetaphosphate, sodium bicarbonate and resinous abrasive materials. In some embodiments, a mixture of abrasives may also be used.

In embodiments, the abrasive is present in an amount from about 0.01% to about 70%, for example, from about 0.01%, 0.1%, 1%, 2%, 5%, 10%, 15%, 20%, 30%, 40%, 50% or to about 70% by weight of the multi-component composition. In some embodiments, the abrasive agent may be present in an amount from about 6% to about 70%, from about 10% to about 50%, or from about 6% to about 70%, from about 20% to about 70%. In some embodiments, such as nasal or oral sprays, oral or vaginal rinses and non-abrasive gel compositions, such as those used in wound healing, may comprise no abrasive.

In aspects, the multi-component composition comprises an alkali metal bicarbonate salt. Alkali metal bicarbonate salts are soluble in water and, unless stabilized, tend to degrade oxidative compounds in an aqueous system. Sodium bicarbonate, also known as baking soda, may be included as an alkali metal bicarbonate salt into the multi-component composition. In embodiments, the alkali metal bicarbonate salt is present in an amount of from about 0.01% to about 70%, for example, from about 0.01%, 0.1%, 1%, 5%, 10%, 20%, 30%, 40%, 50%, 60%, or to about 70% by weight of the multi-component composition. In some other embodiments, the alkali metal bicarbonate salt may be in an amount from about 0.5% to about 70%, from about 1% to about 50%, or from about 5% to about 50%.

In aspects, the multi-component composition further comprises additional agents which reduce dental plaque, tartar and calculus from teeth. In embodiments, the additional agents comprise zinc ions, a cationic material, such as guanides and quaternary ammonium compounds, as well as non-cationic compounds such as halogenated salicylanilides. In some embodiments, an anti-calculus agent is provided, and may be comprised of a pyrophosphate ion source such as pyrophosphate salts. The pyrophosphate salts may include in the multi-component composition may include di-alkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms may be used. In embodiments, the pyrophosphate salt may be present in one of three ways: predominately dissolved, predominantly undissolved, or a mixture of dissolved and undissolved pyrophosphate. In embodiments, the multi-component composition comprises a mixture of dissolved and undissolved pyrophosphate salts. Polyolefin phosphates include those wherein the olefin group contains 2 or more carbon atoms. Other useful materials include synthetic anionic polymers, including poly-acrylates and copolymers of maleic anhydride or acid and methyl vinyl ether (e.g., Gantrez®), as well as, e.g., polyamino propane sulfonic acid (AMPS), zinc citrate trihydrate, poly-phosphates (e.g., tripolyphosphate; hexametaphosphate), diphosphonates (e.g., EHDP; AHP), polypeptides (such as polyaspartic and polyglutamic acids), and mixtures thereof.

In embodiments, the anti-calculus agent may be present in an amount of from about 0.01% to about 50%, for example, from about 0.01%, 0.1%, 1%, 5%, 10%, 15%, 20%, 25%, 30%, 40%, or to about 50% by weight of the multi-component composition. In other embodiments, the anti-calculus agent may be present in an amount from about 0.5% to about 25%, from about 1% to about 25%, or from about 5% to about 50%.

In aspects, a multi-component composition comprises a coloring agent. Preferably, the consumer goodness quality of coloring are not degraded by the oxidative compounds and vice versa. Coloring enables the consumer to more readily ascertain usage and dosage. Certain colors of the composition may be deemed undesirable for certain anal, aural, ocular, oral or urogenital applications. In embodiments, a coloring agent includes, FD&C Blue No. 1 or titanium dioxide. Suitable coloring agents include those that are stable and do not degrade in the presence of the oxidative compounds and do not degrade oxidative compounds. In embodiments, the coloring agent may be in an amount of from about 0.01% to about 10%, for example, from about 0.01%, 0.1%, 1%, 2%, 3%, 4%, 5%, 6%, 7%, 8%, or to about 10% by weight or volume of the multi-component composition. In other embodiments, the coloring agent may be in an amount from about 0.5% to about 10%, from about 1% to about 10%, or from about 0.01% to about 2%, or from 0.8% to about 1.1%.

In aspects, a multi-component composition comprises a cooling and/or warming agent. Suitable cooling and/or warming agents may be those that are stable and do not degrade the presence of the oxidative compound within the compositions, such as those described in U.S. 2017/0877199 to Patton.

In aspects, the multi-component composition further comprises a flavoring agent and/or flavoring systems. Suitable flavoring agents include those that are stable and do not degrade in the presence of the oxidative compounds and do not degrade oxidative compounds. Suitable flavoring systems may include an emulsified flavoring agent for protecting the flavoring agent from degradation. Suitable flavoring systems include those that are taught by U.S. 2012/0164084. In some embodiments, a flavoring agent comprises menthol, mint oil, emulsified mint oil, bubblegum flavor, watermelon flavor or different types of berry flavor. In embodiments, the flavoring agent may be present in an amount of from about 0.01% to about 10%, for example, from about 0.01%, 0.1%, 1%, 2%, 3%, 4%, 5%, 6%, 7%, 8%, or to about 10% by weight or volume of the multi-component composition. In some other embodiments, the flavoring agent may be in an amount from about 0.25% to about 1.2%, from about 1.1% to about 10%, or from about 1.1% to about 7.5%.

In aspects, the multi-component composition comprises a sweetening agent. Suitable sweetening agent may be stable and not degrade in the presence of oxidative compounds or degrade oxidative compounds. In embodiments, the sweetening agent comprises sucrose, aspartame, acesulfame, stevia, saccharin; saccharin salts, especially sodium saccharin; sucralose, sodium cyclamate, and mixtures thereof. In some embodiments, sweetening agents that are polyhydroxy alcohols such as xylitol, mannitol, and sorbitol. In embodiments, a multi-component composition is free of polyhydroxy sweeteners such as xylitol, mannitol, and sorbitol. In embodiments, a sweetening agent comprises sucrose, sucralose, acesulfame, aspartame, cyclamate, or saccharin. In some embodiments, the sweetener may be in an amount of from about 0.01% to about 0.5%, for example, from about 0.01%, 0.02%, 0.05%, 0.1%, 0.2%, 0.3%, 0.4%, or to about 0.5% by weight or volume of the multi-component composition. In some other embodiments, the sweetener may be in an amount from about 0.05% to about 0.5%, from about 0.1% to about 0.2%, from about 0.01% to about 0.5%, or from 0.01% to about 0.2%.

In aspects, a multi-component composition further comprises one or more humectants. Suitable humectants include those that include at least one of the following: serves to keep pastes and gels and suspensions from hardening or losing their consumer goodness qualities when exposed to air, to add to the compositions a moist feel to the consumer goodness qualities and, for particular humectants orally applied, to impart desirable sweetness of flavor, such as toothpaste compositions. In embodiments, the humectant comprises polyhydroxy alcohols, including arabitol, erythritol, glycerol, maltitol, mannitol, sorbitol, and/or xylitol. Polyhydroxy alcohols are commonly accepted excipients and most belong to the Generally Recognized as Safe (GRAS) category for pharmaceutical, cosmetic, and food products. Other compounds which provide moist texture for suitable formulations may also be used. Though humectants such as glycerol, sorbitol and other polyhydroxy compounds have been known to cause degradation of oxidative compounds when comprised in the same single phase, in accordance with various aspects, it has been discovered that a single phase multi-component composition comprising the combination of an oxidative compound and an aliphatic anionic compound (e.g., an N-acyl sarcosinate compound) that exhibit humectant type in terms of providing consistency to the composition and surface active properties may not experience significant degradation of the oxidative compound. In various embodiments, sorbitol may be a humectant comprised in the multi-component composition.

In some embodiments, the humectant may be present in an amount of from about 0.001% to about 70%, for example, from about 0.001%, 0.01%, 1%, 2%, 5%, 10%, 20%, 30%, 40%, 50%, or to about 70% by weight or volume of the multi-component composition. In some other embodiments, the humectant may be in an amount from about 1% to about 15%, from about 15% to about 55%, or from about 25% to about 55%.

In aspects, the multi-component composition comprises a fluoride ion source. In embodiments, the multi-component composition includes free fluoride ions or covalently bound fluorine in a form that may be hydrolyzed by oral enzymes to yield free fluoride ions. Free fluoride ions comprise sodium fluoride, silver diamine fluoride, stannous fluoride, or indium fluoride. Covalently bound fluorine, which can be enzymatically hydrolyzed to yield free fluoride, may be provided by sodium monofluorophosphate. In various embodiments, sodium fluoride may be comprised in the multi-component composition as the source of free fluoride ions. If a fluoride ion source is used as a component in a multi-component composition, a "fluoride ion source" as disclosed in, U.S. Pat. Appl. No. 2011/0318282 may be preferred. In embodiments, it has been surprisingly found that the presence of a fluoride ion source in a single phase multi-component composition, comprising for example the combination of an oxidative compound and an aliphatic anionic compound (e.g., an N-acyl sarcosinate compound), such composition may resist significant degradation of the oxidative compound and promote shelf-life and shelf-stability. In embodiments, a multi-component composition comprises a fluoride ion source, an aliphatic anionic compound (e.g., an N-acyl sarcosinate compound), and an oxidative compound. The composition may remain stable for a reasonable period of time. The composition may maintain the capacity for the oxidative compounds of the composition to react or activate upon use. The composition may enhance the capacity for the oxidative compounds to increase penetration of bacteria and biofilms as opposed to comparable compositions not containing an aliphatic anionic compound. In some embodiments, the fluoride ion source comprises at least one of an indium fluoride, sodium fluoride, silver diamine fluoride, stannous fluoride, or sodium monofluorophosphate.

In embodiments, a multi-component composition further comprises a source of fluoride ion providing fluoride ions from about 0 ppm to about 5000 ppm, or from about 50 ppm to about 3500 ppm, from about 500 ppm to about 3500 ppm. In some embodiments, the fluoride ion source may be in an amount of from about 0% to about 2.0%, for example, from about 0.01%, 0.1%, 0.15%, 0.2%, 0.3%, 0.4%, 0.5%, 0.6%, 0.7%, 0.8%, or to about 2.0% by weight or volume of the multi-component composition. In other embodiments, the fluoride ion source may be in an amount from about 0.0% to about 0.03%, from about 0.0% to about 0.7%, from about 0.1% to about 0.8%, from about 0.01% to about 0.07%, or from about 0.0% to about 0.8%. A composition is referred as fluoride-free when the source of fluoride ion source is 0% or when the composition is essentially free of fluoride as described herein.

In aspects, a multi-component composition further comprises a thickening or binding agent. The thickening or binding agent may provide desired consumer goodness qualities appropriate to the multi-component composition, such as the desirable consistency or viscosity of the composition, to provide desirable dosage and at a rate of release desired of the oxidative compounds upon use, and to adhere to hard or soft tissues in a topical application. Examples of thickening or binding agents include carboxyvinyl polymers, seaweed derivatives such as carrageenan, hydroxyethyl cellulose, laponite, powdered polyethylene, and water soluble salts of cellulose ethers such as sodium carboxymethylcellulose and sodium carboxymethyl hydroxyethyl cellulose. Natural gums such as gum karaya, guar gum, xanthan gum, gum arabic, and gum tragacanth can also be used. Colloidal magnesium aluminum silicate or finely divided silica may be used as part of the thickening or binding agent to further improves texture. Higher concentrations of thickening agents can be used for chewing gums, lozenges (including breath mints), sachets, non-abrasive gels and gels intended for use in wound-healing, vaginal or oral disease.

In some embodiments, the thickening or binding agent may be present in an amount of from about 0% to about 15%, for example, from about 0.01%, 0.1%, 1%, 2%, 3%, 4%, 5%, 6%, 7%, 8%, or to about 15% by weight or volume of the multi-component composition. In some other embodiments, the thickening or binding agent may be in an amount from about 0.1% to about 15%, from about 2.0% to about 10%, from about 4% to about 8%, from about 1.0% to about 4.0%, or from about 5.0% to about 7.0%.

In aspects, the multi-component composition further comprises a whitening and/or opacifying agent. In embodiments, the whitening and/or opacifying agent comprises a non-hydrogen peroxide whitening agent. For example, titanium dioxide may be included to a multi-component composition to achieve whiteness or opaqueness of the multi-component composition. In various embodiments, a whitening and/or opacifying agent comprises a peroxide, metal chlorite, perborate, percarbonate, peroxyacid, persulfate, and combinations thereof. Suitable peroxide compounds include hydrogen peroxide, urea peroxide (carbamide peroxide), calcium peroxide, and mixtures thereof. In various embodiments, the multi-component composition may be essentially free of glycerin and/or polyhydroxy compounds. In embodiments, the whitening and/or opacifying agent may be present in an amount of from about 0% to about 20%, for example, from about 0.01%, 0.1%, 2%, 4%, 6%, 8%, 10%, 12%, 14%, 16%, or to about 20% by weight or volume of the multi-component composition. In some other embodiments, the fluoride ion source may be in an amount from about 0.01% to about 20%, from about 0.5% to about 10%, or from about 4% to about 7%.

In aspects, the multi-component composition further comprises water. Water may provide the remaining weight percent of the multi-component compositions (i.e., the weight percent not attributed to the other components described herein). Water employed in the multi-component compositions used as commercially suitable topical compositions can be of low ion content and essentially free of organic impurities. Water can comprise up to about 98% of the composition, particularly for mouthwashes, mouth rinses and mouthwashes, oral and nasal sprays, vaginal douches, and soaks, and preferably from about 5% to about 60%, by weight of the aqueous compositions herein. These amounts of water include the free water which is added to the composition plus that which is introduced with other materials added to the composition. Some embodiments described herein the multi-compound composition include powders, lozenges and chewing gum, are of course substantially dry or contain only a small amount of water.

In aspects, the multi-component composition further comprises a surfactant. Surfactants may be anionic, cationic, non-ionic, or amphoteric (zwitterionic). These may be useful as foaming agents in oral care, cosmetic, healthcare, and pharmaceutical products. Such foaming agents may also useful in the retention of sanitizing and moisturizing agents in skin care products, such as shaving creams and foams. In embodiments, the surfactant may be in an amount of from about 0% to about 15%, for example, from about 0.01%, 0.1%, 1%, 2%, 3%, 4%, 5%, 6%, 7%, 8%, or to about 15% by weight or volume of the multi-component composition. In some other embodiments, the surfactant may be in an amount from about 0.1% to about 15%, from about 2.0% to about 10%, or from about 4% to about 8%.

In aspects, the multi-component composition further comprises a desensitizing agent. The desensitizing agent may be provided for temporary relief from pain to hard or soft tissues. In embodiments, the desensitizing agent comprises compounds such as strontium chloride, strontium acetate, arginine, hydroxyapatite, nano-hydroxyapatite (nano-HAp), calcium sodium phosphosilicate, potassium chloride or potassium nitrate. In various embodiments, the compositions may be essentially free of compounds, such as sodium lauryl sulfate, that irritate sensitive body cavities such as anal, nasal, ocular, oral, and urogenital. Examples of sensitivities and resultant diseases oral cavity include canker sores, oral mucositis, and dry mouth.

In aspects, the multi-component composition further comprises a preservative. In embodiments, the preservative comprises a methyl paraben, propyl paraben, disodium EDTA, benzyl alcohol, benzoic acid, or sodium benzoate. In embodiments, the preservative may be present in an amount of from about 0% to about 2%, for example, 0.01%, 0.1%, 1%, or 2% by weight or volume of the multi-component composition. In other embodiments, the surfactant may be in an amount from about 0.1% to about 0.15%, from about 0.2% to about 1%, from about 0.01% to 0.5%, or from about 0.4% to about 0.8%.

In embodiments, the multi-component composition does not contain a polyhydroxy compound. Polyhydroxy compounds are known to react and degrade oxidative compounds and compounds, such as stabilized chlorine dioxide, and therefore, may be excluded from the multi-component composition. Polyhydroxy compounds may include glycerin, alcohols, polyethylene glycols, xylitol, and sorbitol.

In embodiments, the multi-component compositions described herein are single-phase composition. In embodiments, the multi-component composition is configured to form a dentifrice. In embodiments, the multi-component composition is configured to form an oral rinse. In embodiments, the multi-component composition is an oral care composition, such as an oral spray, oral gel, denture or dental appliance soak, toothbrush soak, or a solution intended for use in an oral irrigation device.

In aspects, the multi-component composition is formulated as a cosmetic. Cosmetic compositions (for example, a solid cosmetic composition, such as a gel, soft-solid or semi-solid (cream), or stick), may be comprised of a base composition containing at least one silicone fluid (for example, silicone liquids such as silicone oils) which is thickened using a siloxane-based polyamide as a gelling agent; a carrier in which cosmetically active materials are incorporated; and at least one active ingredient to provide the activity for such cosmetic composition. In embodiments, the cosmetic compositions are transparent (clear), including solid transparent (clear) compositions. In embodiments, the cosmetic composition is formulated that the final composition is opaque. In embodiments, the cosmetic composition is formulated so that the final composition is not-transparent.

In embodiments, the cosmetic may further comprise one or more additional agents as carriers, selected from one or more of abrasive polishing materials, alkali metal bicarbonate salts, analgesic and anesthetic agents, anti-inflammatory agents, anti-malodor agents, anti-microbial agents, anti-plaque agents, and anti-viral agents, biofilm disrupting, dissipating or inhibiting agents, buffers and buffering systems, cellular redox modifiers and antioxidants, coloring agents and coloring systems, cytokine receptor antagonists, dental anti-calculus agents, hormones, metalloproteinase inhibitors, immune-stimulatory agents, lipopolysaccharide complexing agents, tissue growth factors, titanium dioxide, vitamins and minerals, and mixtures thereof. It is recognized that in certain forms, such as combinations of therapeutic agents in the same delivery system, may be useful to obtain an optimal effect. In some embodiments, the multi-component composition may be combined with one or more such agents in a single phase delivery system to provide combined effectiveness, while maintaining the stability of the oxidative compound (e.g., stabilized chlorine dioxide).

In embodiments, the multi-component composition may be specifically formulated for use in humans and animals, for example in the form of rinses, gels, pastes, creams, washes, sprays, lozenges, therapeutic floss, tape, patches, compresses, or strips, for use in skin care, oral care, urogenital care, foot care, wound healing and as a solution used in irrigation devices for use in the oral and other body cavities.

In aspects, the multi-component composition has consumer goodness qualities. In embodiments, ingredients are selected for an oral care composition that achieves a desirable range of viscosity to ensure product manufacturability, applicability, stability, and quality, as well as consumer acceptance. In embodiments, the multi-component composition may be phase stabile. Phase stability may refer to an oral care composition visually (i.e., to the unaided eye) having no liquid separation from the composition's body over a defined period of time under ambient conditions. Such phase stable multi-component compositions may resist syneresis. For example, a toothpaste embodiment herein may be less abrasive on teeth than a similar composition without the inclusion of aliphatic anionic compounds. In a liquid embodiment, such as an oral rinse, consumer goodness qualities may comprise where the composition retains clarity (clear, water-like appearance); however clarity is not limited by the presence of a color in the composition if a color is intended. In another embodiment, a vaginal douche embodiment should not sting, stain, burn or otherwise cause irritation to the user, has a viscosity that enables ease of use, and has a pleasing fragrance or no fragrance at all following use. Consumer goodness qualities of various embodiments herein may vary for use with other animals. For example, an oral rinse for dogs may have preferably a meat flavor while one for humans may have a mint flavor.

In aspects, the multi-component composition is suitable for a variety of indications, including treatment and prevention of oral or vaginal malodor, as well as ocular, nasal and skin care and other topical uses. Suitable topical indications include anal, aural, oral, nasal, ocular, urogenital, foot-care and skin-care conditions and diseases. The composition may be suitable for select indications, including antimicrobial, antiseptic, antioxidant, bactericidal and bacteriostatic, biofilm penetration, biofilm dissipation and reduction, coagulant, deodorant, desensitizing, disinfectant, fungicidal and fungistatic, herbicidal, tissue damage reduction, bleaching, stain removal, and tooth whitening. Compositions herein are suitable for use in a variety of forms, including rinses, gels, pastes, creams, washes, sprays, lozenges, floss, tape, patches, bandages, compresses, wraps, and strips.

In aspects, the multi-component composition maintains stability and consumer goodness. In embodiments, stability and consumer goodness is maintained from manufacture of the composition through about twelve (12) months of storage under ambient conditions. In embodiments, the multi-component composition may exhibit no more than 10% loss in stabilized chlorine dioxide in three (3) months at 40±2° C. and 75%±5% relative humidity (RH) which may be equivalent to twelve (12) months of storage at room temperature. In embodiments, the multi-component composition may exhibit no more than 20% loss in stabilized chlorine dioxide in in three (3) months at 40±2° C. and 75%±5% relative humidity (RH). In embodiments, the multi-component composition may exhibit no more than 30% loss in stabilized chlorine dioxide in three (3) months at 40±2° C. and 75%±5% relative humidity (RH). In some embodiments, the multi-component composition may exhibit no more than 40% loss in stabilized chlorine dioxide in three (3) months at 40±2° C. and 75%±5% relative humidity (RH) In another embodiment, storage of the composition under accelerated conditions (typically 40±2° C. and 75%±5% relative humidity, RH) can project real time suitability of a composition for consumer use, anticipating the time of manufacture, transit from point of manufacture to wholesaler, from wholesaler to retailer, from retailer to consumer, plus the anticipated storage time by the consumer as the product is consumed.

Exemplary Composition I: Toothpaste Embodiment

Various single-phase oral care toothpaste compositions may comprise: from about 0.005% to about 2.0% a chlorite ion source such as sodium chlorite, from about 0.7% to about 4.2% a base such as disodium hydrogen phosphate or trisodium phosphate, from about 0.05% to about 2.20% an acid or a buffering salt on the acidic side, such as sodium dihydrogen phosphate, citric acid, or acetic acid, from about 0.2% to about 5.0% an N-acyl sarcosinate compound, such as sodium lauroyl sarcosinate, sodium cocoyl sarcosinate, or sodium myristoyl sarcosinate, from about 0.8% to about 1.1% coloring agent such as FD&C Blue No. 1 or titanium dioxide, from about 1.0% to about 4.0% gelling agent such as gelatin, pectin, guar gum, xanthan gum, other natural or synthesized gums, cellulose gum or sodium carboxymethyl cellulose, from about 20.0% to about 70.0% abrasive agent such as hydrated silica, calcium hydrogen phosphate, alumina, sodium bicarbonate, from about 0.05% to about 0.5% sweetening agent such as sucrose, sucralose, acesulfame, aspartame, cyclamate, or saccharin, from about 0.025% to about 1.2% flavoring agent such as menthol, mint oil, emulsified mint oil, tropical fruit, watermelon, bubblegum, strawberry or berry flavor, from about 0.0% to about 0.8% fluoride ion source or source of releasable fluoride ion, such as sodium fluoride, silver diamine fluoride, sodium monofluorophosphate, or stannous fluoride, and water to 100%, thereby maintaining the final pH in the range of about 6.0 to about 8.0. For preparing fluoride-free toothpaste compositions, the fluoride ion source is eliminated from the composition and the quantity of water is adjusted accordingly.

Exemplary Composition II: Oral Care Gel Embodiment

Various single-phase oral care gel compositions may comprise: from about 0.005% to about 2.0% chlorite ion source such as sodium chlorite, from about 0.7% to about 4.2% a base, such as disodium hydrogen phosphate or trisodium phosphate, from about 0.05% to about 2.20% an acid or a buffering salt on the acidic side, such as phosphoric acid, sodium dihydrogen phosphate, citric acid, or acetic acid, from about 0.2% to 5.0% an N-acyl sarcosinate compound, such as sodium lauroyl sarcosinate, sodium cocoyl sarcosinate, or sodium myristoyl sarcosinate, from about 5.0% to about 7.0% gelling agent such as gelatin, pectin, xanthan gum, guar gum, cellulose gum, other natural or synthesized gums, or sodium carboxymethyl cellulose, from about 0.05% to about 0.5% sweetening agent such as sucrose, acesulfame, aspartame, sucralose, or saccharin, from about 0.025% to about 1.2% flavoring agent such as menthol, mint oil, emulsified mint oil, bubblegum flavor, strawberry, fruity, watermelon or berry flavor, from about 0.01% to about 0.8% fluoride ion source such as sodium fluoride stannous fluoride, or sodium monofluorophosphate, and water to 100% thereby maintaining the final pH in the range of about 6.0 to about 8.0. For preparing fluoride-free gel compositions, the fluoride ion source is eliminated from the composition and the quantity of water is adjusted accordingly. The composition may comprise a buffering system and/or a flavoring system as described herein.

Exemplary Composition III: Oral Rinse Embodiment

Various single-phase oral care rinse compositions may comprise: from about 0.005% to about 2.0% of chlorite ion source such as sodium chlorite, from about 0.2% to about 4.0% a base, such as disodium hydrogen phosphate or trisodium phosphate, from about 0.04% to about 2.10% an acid or a buffering salt on the acidic side, such as sodium dihydrogen phosphate, phosphoric acid, citric acid or acetic acid, from about 0.01% to about 1.0% an N-acyl sarcosinate compound such as sodium lauroyl sarcosinate, sodium cocoyl sarcosinate, or sodium myristoyl sarcosinate, from about 0.01% to about 0.2% sweetening agent such as sucrose, acesulfame, aspartame, cyclamate, sucralose, or saccharin, from about 0.025% to about 1.2% flavoring agent such as menthol, mint oil, emulsified mint oil, tropical fruit, bubblegum, watermelon, strawberry or berry flavor, from about 0.0% to about 0.07% fluoride ion source or source of releasable fluoride ion, such as sodium fluoride, stannous fluoride, sodium monofluorophosphate, or acidulated phosphate fluoride, and water to 100% thereby maintaining the final pH in the range of about 6.0 to about 8.0. For preparing fluoride-free oral rinse compositions, the fluoride ion source is eliminated from the composition and the quantity of water is adjusted accordingly. Similarly, for preparing fluoride-free and unflavored oral rinse compositions, the fluoride ion source and the flavoring agents are eliminated from the composition. The composition may comprise a buffering system and/or a flavoring system as described herein.

Exemplary Composition IV: Oral Spray Embodiment

Various oral care spray formulation may comprise: from about 0.005% to about 2.0% chlorite ion source such as sodium chlorite, from about 0.05% to about 0.5% a base such as disodium hydrogen phosphate, sodium citrate, or trisodium phosphate, from about 0.01% to about 0.05% an acid or a buffering salt on the acidic side, such as phosphoric acid, citric acid, acetic acid, or sodium dihydrogen phosphate, from about 0.01% to about 1.0% an N-acyl sarcosinate compound such as sodium lauroyl sarcosinate, sodium cocoyl sarcosinate, or sodium myristoyl sarcosinate, from about 0.01% to about 0.5% sweetening agent such as sucrose, acesulfame, aspartame, cyclamate, sucralose, or saccharin, from about 1.1% to about 7.5% flavoring agent such as menthol, mint oil, emulsified mint oil, watermelon, bubblegum, tropical fruit, strawberry or berry flavor, from about 0.5% to 7.0% dispersing agent such as a polysorbate, from 0.01% to 0.5% preservative, such as methyl paraben, propyl paraben, disodium EDTA, sodium benzoate, or combination thereof and water to 100% thereby maintaining the final pH in the range of about 6.0 to about 8.0. The composition may comprise a buffering system and/or a flavoring system as described herein.

Exemplary Composition V: Wound-Healing Gel/Ointment Embodiment

Various single-phase oral care gel compositions may comprise: from about 0.005% to about 2.0% chlorite ion source such as sodium chlorite, from about 0.7% to about 2.2% a base such as disodium hydrogen phosphate or trisodium phosphate, from about 0.06% to about 0.20% an acid or a buffering salt on the acidic side, such as sodium dihydrogen phosphate, citric acid, or acetic acid, from about 0.5 to 5.0% an N-acyl sarcosinate compound, such as sodium lauroyl sarcosinate, sodium cocoyl sarcosinate, or sodium myristoyl sarcosinate, from about 5.0% to about 7.0% gelling agent such as gelatin, pectin, guar gum, xanthan gum, cellulose gum, or sodium carboxymethyl cellulose, from about 0.025% to about 1.2% a cooling agent, such as menthol or emulsified mint oil, from about 0.1% to about 10% an emollient agent, such as mineral oil, from about 0.1% to about 5% a suspending or emulsifying agent, such as a polysorbate, and water to 100% thereby maintaining the final pH in the range of about 6.0 to about 8.0. The composition may comprise a buffering system and/or a flavoring system as described herein.

Exemplary Composition VI: Vaginal Douche Embodiment

Various single-phase vaginal douche compositions, preferably, comprise: from about 0.005% to about 2.0% a chlorite ion source such as sodium chlorite, from about 0.2% to about 2.0% a base such as sodium bicarbonate, disodium hydrogen phosphate or trisodium phosphate, from about 0.00% to about 0.10% an acid or a buffering salt on the acidic side, such as boric acid, citric acid, acetic acid, or sodium dihydrogen phosphate, from about 0.001% to about 1.0% an N-acyl sarcosinate compound such as sodium lauroyl sarcosinate, sodium cocoyl sarcosinate, or sodium myristoyl sarcosinate, from about 0.1% to about 10% an emollient agent, such as mineral oil, from about 0.1% to about 5% a suspending or emulsifying agent, such as a polysorbate or poloxamer, from 0.01% to 20% a fragrance, such as rose, lilac or geranium fragrance, or other proprietary fragrance compositions provided by commercial suppliers of fragrances, and water to 100% thereby maintaining the final pH in the range of about 6.0 to about 8.0. For preparing fragrance-free vaginal douche compositions, the fragrance source is eliminated from the composition and the quantity of water is adjusted accordingly. The composition may comprise a buffering system and/or a flavoring system as described herein.

Methods for Preparing Exemplary Compositions

In preparing compositions as described herein and where the Exemplary Composition is a paste or gel, the gelling agents are dissolved in water. Pharmaceutically-acceptable buffering compounds of the appropriate type and concentration such as weak acid and its conjugate base or weak base and its conjugate acid are then added to the solution of gelling agent in water until the preferred final pH range of 6.0 to 8.5 is achieved. Then the solution containing a buffering system may be mixed with the chlorite ion source in an aqueous solution. The remaining ingredients, e.g. humectants, sweetening agents, coloring agents, abrasive agents, fluoride ion source, flavoring agent(s), emollient agents, suspending or emulsifying agents, additional deionized or purified water, and other ingredients as described above and as applicable, are added one by one in appropriate amounts to maintain the final pH of the overall formulation in the range of 6.0 to 8.5. The N-acyl sarcosinate may be added as a last ingredient while preparing the composition. All compounding may occur at ambient temperatures to maintain the stability of the composition.

Similarly, in preparing a multi-component composition where the Exemplary Composition is a liquid, a rinse or an aerosol spray, the base compound selected may be dissolved in deionize or purified water in a separate preparation. This solution may be mixed with the chlorite ion source in an aqueous solution. The remaining ingredients, e.g. sweetening agents, flavoring agents, fluoride ion source, additional deionized or purified water, and/or other ingredients as described above and as applicable, are added one by one in appropriate amounts. The N-acyl sarcosinate such as sodium lauroyl sarcosinate may be added prior to adding the weak acid while preparing the composition. The appropriate amount of weak acid may be dissolved in water and the appropriate quantity may be mixed with the composition to maintain the final pH of the overall formulation in the range of 6.0 to 8.5. The base compound and the weak acid of the composition constitute the buffering system as defined herein. All compounding may be required to occur at ambient temperatures to maintain the stability of the composition.

In preparing a multi-component composition where the Exemplary Composition is a liquid spray, the method for preparation follows the method for oral rinse composition taught above, wherein additional ingredients such as dispersing agents, humectants, or preservatives are mixed with the composition prior to adjusting the pH of the final composition in the range of 6.0 to 8.5.

Example 1. Formulations of a Toothpaste Embodiment

Various compositions of Exemplary Composition I were formulated and tested below. Toothpaste compositions and ingredients thereof tested (Toothpaste A through H) are summarized in Table 1. Table 2 provides a summary of the percentage weight to total weight of each ingredient in Toothpastes A to H.

TABLE 1

Comparison Toothpaste Compositions Ingredients

| Ingredient | Toothpaste A | Toothpaste B | Toothpaste C | Toothpaste D | Toothpaste E | Toothpaste F | Toothpaste G | Toothpaste H |
|---|---|---|---|---|---|---|---|---|
| Chlorite Ion Source | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide | Stabilized Chlorine Dioxide |
| Buffering System or pH adjusting agent | $Na_3PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ | $Na_2HPO_4$ + $NaH_2PO_4$ |
| Humectant(s) | Glycerin + Sorbitol | Sorbitol | — | — | — | — | Sorbitol | — |
| Aliphatic anionic compound | — | — | Sodium Lauroyl Sarcosinate | Sodium Lauroyl Sarcosinate | Sodium Cocoyl Sarcosinate | Sodium Myristoyl Sarcosinate | Sodium Lauroyl Sarcosinate | — |
| Source of Fluoride | — | Sodium Fluoride | Sodium Fluoride | — | Sodium Fluoride | Sodium Fluoride | Sodium Fluoride | Sodium Fluoride |
| Thickening Agent | Cellulose Gum | Cellulose Gum | Cellulose Gum | Cellulose Gum | Cellulose Gum | Cellulose Gum | Cellulose Gum | Cellulose Gum |
| Coloring Agent (whitening) | Titanium Dioxide | Titanium Dioxide | Titanium Dioxide | Titanium Dioxide | Titanium Dioxide | Titanium Dioxide | Titanium Dioxide | Titanium Dioxide |
| Abrasive Agent | Hydrated Silica | Hydrated Silica | Hydrated Silica | Hydrated Silica | Hydrated Silica | Hydrated Silica | Hydrated Silica | Hydrated Silica |
| Flavoring Agents(s) | Peppermint oil + Spearmint oil + Menthol Crystals | Peppermint oil + Menthol Crystals | Peppermint oil + Menthol Crystals | Peppermint oil + Menthol Crystals | Peppermint oil + Menthol Crystals | Peppermint oil + Menthol Crystals | Peppermint oil + Menthol Crystals | Peppermint oil + Menthol Crystals |
| Sweetener | Sodium Saccharin | Sucralose | Sucralose | Sucralose | Sucralose | Sucralose | Sucralose | Sucralose |
| Water | Water | Water | Water | Water | Water | Water | Water | Water |

Note:
$Na_3HPO_4$: Trisodium phosphate.
$Na_2HPO_4$: Disodium hydrogen phosphate.
$NaH_2PO_4$: Sodium dihydrogen phosphate.

TABLE 2

Toothpaste Compositions

| Ingredient | Toothpaste A (% w/w) | Toothpaste B (% w/w) | Toothpaste C (% w/w) | Toothpaste D (% w/w) | Toothpaste E (% w/w) | Toothpaste F (% w/w) | Toothpaste G (% w/w) | Toothpaste H (% w/w) |
|---|---|---|---|---|---|---|---|---|
| Stabilized Chlorine Dioxide | 0.14 | 0.14 | 0.14 | 0.14 | 0.14 | 0.14 | 0.14 | 0.14 |
| Trisodium phosphate | 1.0 | — | — | — | — | — | — | — |
| Disodium hydrogen phosphate + Sodium dihydrogen phosphate | — | 1.6 | 2.4 | 2.4 | 2.4 | 2.4 | 2.4 | 2.4 |

TABLE 2-continued

Toothpaste Compositions

| Ingredient | Toothpaste A (% w/w) | Toothpaste B (% w/w) | Toothpaste C (% w/w) | Toothpaste D (% w/w) | Toothpaste E (% w/w) | Toothpaste F (% w/w) | Toothpaste G (% w/w) | Toothpaste H (% w/w) |
|---|---|---|---|---|---|---|---|---|
| Glycerin | 10.0 | — | — | — | — | — | — | — |
| Sorbitol | 31.2 | 15.0 | — | — | — | — | 15.0 | — |
| Sodium Lauroyl Sarcosinate | — | — | 2.5 | 2.5 | — | — | 2.5 | — |
| Sodium Cocoyl Sarcosinate | — | — | — | — | 2.5 | — | — | — |
| Sodium Myristoyl Sarcosinate | — | — | — | — | — | 2.5 | — | — |
| Sodium Fluoride | — | 0.24 | 0.24 | — | 0.24 | 0.24 | 0.24 | 0.24 |
| Cellulose Gum | 1.2 | 1.9 | 1.9 | 1.9 | 1.9 | 1.9 | 1.9 | 1.9 |
| Titanium Dioxide | 0.95 | 0.95 | 0.95 | 0.95 | 0.95 | 0.95 | 0.95 | 0.95 |
| Hydrated Silica | 26.0 | 26.0 | 26.0 | 26.0 | 26.0 | 26.0 | 26.0 | 26.0 |
| Peppermint oil + Menthol Crystals | 0.9 | 0.9 | 0.9 | 0.9 | 0.9 | 0.9 | 0.9 | 0.9 |
| Sucralose | — | 0.1 | 0.2 | 0.2 | 0.2 | 0.2 | 0.2 | 0.2 |
| Sodium saccharin | 0.27 | — | — | — | — | — | — | — |
| Water | 28.34 | 53.17 | 64.77 | 65.01 | 64.77 | 64.77 | 49.77 | 67.27 |

Example 2: Accelerated Stability Testing of Toothpastes A, B, C. And D

Toothpaste A was prepared following the teachings of U.S. Pat. Nos. 5,200,171, 5,348,734, and 5,489,435. pH of the composition containing stabilized chlorine dioxide was adjusted using only one pH adjusting agent, which is a phosphate salt, trisodium phosphate. Toothpaste A contained glycerol and sorbitol as humectants.

Toothpaste B was prepared following the teachings of U.S. Patent Application U.S. 2011/0318282. Toothpaste B contained sorbitol as humectant but did not contain glycerol.

Toothpastes C, E, and F were prepared following the teaching as described herein and according to Exemplary Composition I, wherein the stabilized chlorine dioxide compositions were free of both glycerol and sorbitol and contained N-acyl sarcosinate, an aliphatic anionic compound, such as sodium lauroyl sarcosinate, sodium cocoyl sarcosinate, and sodium myristoyl sarcosinate, respectively.

Toothpaste D was prepared following the teaching as described herein, that is, that it was identical to Toothpaste C except for the absence of any fluoride ion source.

Toothpaste G was prepared following the teaching as described herein and according to Exemplary Composition I, wherein the multi-component composition contained sorbitol and sodium lauroyl sarcosinate.

Toothpaste H was prepared following the teaching as described herein and according to Exemplary Composition I, wherein the stabilized chlorine dioxide composition was free of sorbitol and an aliphatic anionic compound.

Accelerated stability testing of Toothpaste A, Toothpaste B, Toothpaste C, and Toothpaste D were performed at 40±2° C. and 70-75% relative humidity ("RH"). The results are summarized in Table 3. Accelerated stability testing at 40° C.±2° C. and 75%±5% RH is a standard accelerated stability test conducted in the pharmaceutical and cosmetic industries (Guidance for Industry: Q1A(R2) Stability Testing of New Drug Substances and Products, FDA, Revision 3 Nov. 2003). Oral care compositions claimed to maintain stable amounts of the chlorite ion at 25° C. for one year or 40° C. for 3 months is described in U.S. Pat. No. 6,696,047. The stability testing of the compositions of Exemplary Composition I adheres to accepted norms of prior art and the pharmaceutical industry.

TABLE 3

Comparison of stability of toothpaste compositions at 40° ± 1° C. and 70-75% RH

| | Initial | 1 Month | | 2 Months | | 3 Months | | 6 months | |
|---|---|---|---|---|---|---|---|---|---|
| Composition | SCD* (%) | SCD (%) | Loss (%) | SCD (%) | Loss (%) | SCD (%) | Loss (%) | SCD (%) | Loss (%) |
| Toothpaste A (Teachings of U.S. Pat. Nos. 5,200,171; 5,348,734; and 5,489,435) | 0.077 | 0.019 | 75.3 | 0.005 | 93.5 | 0.0025 | 96.7 | NT§ | NT |

TABLE 3-continued

Comparison of stability of toothpaste compositions at
40° ± 1° C. and 70-75% RH

| Composition | Initial SCD* (%) | 1 Month SCD (%) | 1 Month Loss (%) | 2 Months SCD (%) | 2 Months Loss (%) | 3 Months SCD (%) | 3 Months Loss (%) | 6 months SCD (%) | 6 months Loss (%) |
|---|---|---|---|---|---|---|---|---|---|
| Toothpaste B (U.S. 2011/031,8828) | 0.114 | 0.097 | 14.9 | 0.072 | 36.8 | 0.049 | 57.0 | NT | NT |
| Toothpaste C (Exemplary Composition I) | 0.12 | 0.12 | 0.0 | 0.11 | 8.3 | 0.10 | 16.6 | 0.09 | 25.0 |
| Toothpaste D (Exemplary Composition I) | 0.12 | 0.11 | 8.3 | 0.11 | 8.3 | 0.10 | 16.6 | 0.08 | 33.3 |

*SCD: Stabilized chlorine dioxide
§NT: Not Tested. The stability study for Toothpastes A and B was discontinued after observing unacceptable loss of 96.7% and 57.0% in 3 months.

As Table 3 shows, Toothpaste C and Toothpaste D provide much greater shelf-life stability than Toothpaste A and Toothpaste B as taught by prior art. Only 16.6% loss of stabilized chlorine dioxide in 3 months was observed for Toothpaste C and Toothpaste D. In contrast, Toothpaste A and Toothpaste B exhibited 96.7% and 57.0% loss of stabilized chlorine dioxide, respectively, in 3 months. The 75.3% loss of stabilized chlorine dioxide from Toothpaste A in 1 month demonstrates that the shelf life stability of Toothpaste A is less than 4 months at room temperature. Similarly, 36.8% loss of stabilized chlorine dioxide from Toothpaste B in 2 months demonstrates that the shelf life of Toothpaste B is less than 8 months at room temperature. Thus, both Toothpaste A and Toothpaste B do not provide shelf life stability of stabilized chlorine dioxide for a reasonable period of time, as defined herein, that is desirable for an over-the-counter consumer product. Importantly, 25.0% and 33.3% losses of stabilized chlorine dioxide in Toothpaste C and Toothpaste D after six months at 40° C., respectively, indicate that Toothpaste C and Toothpaste D have a shelf life of at least 24 months (2 years) at room temperature.

Example 3. Accelerated Stability Testing of Toothpastes A-H

Without being limited by scientific theory, the stability demonstrated by Toothpaste C and Toothpaste D is believed to be attributed to the inclusion of an aliphatic anionic compound in the multi-component composition, such as sodium lauroyl sarcosinate. The achieved stability of the chlorine dioxide in Toothpaste C and Toothpaste D is an unexpected result based on the tendency of chlorine dioxide to decompose or react with other components. Of note, the toothpaste embodiments, as tested, demonstrated a stable shelf-life for a single-phase composition comprising an oxidative compound, an aliphatic anionic compound, a buffering system, and carriers of the composition. Toothpaste C and D were stable for a reasonable period of time, e.g., from the time of compounding to a normal time of usage for topical OTC oral care products. The discovery of the effect of sodium lauroyl sarcosinate in increasing the stability of stabilized chlorine dioxide in Toothpaste C and Toothpaste D of Exemplary Composition I compared to Toothpaste A and Toothpaste B of the prior art is an unexpected result.

Further experiments were performed to verify the stabilizing benefit of an N-acyl sarcosinate with an oxidative compound. Toothpaste compositions containing N-acyl sarcosinate compounds such as sodium lauroyl sarcosinate (Toothpaste C), sodium cocoyl sarcosinate (Toothpaste E), and sodium myristoyl sarcosinate (Toothpaste F), as discussed in Exemplary Composition I were prepared and tested for their stability. Additionally, toothpaste containing N-acyl sarcosinate and sorbitol (Toothpaste G) and that does not contain sorbitol as well as N-acyl sarcosinate (Toothpaste H) were prepared and tested for their stability. The results are summarized in Table 4.

TABLE 4

Comparison of stability of Toothpastes prepared with different N-acyl sarcosinate compounds at 40° ± 1° C. and 70-75% RH

| Composition | Humectant | N-Acyl Sarcosinate | Initial SCD* (%) | 2 Month SCD (%) | 2 Month Loss (%) | 3 Month SCD (%) | 3 Month Loss (%) |
|---|---|---|---|---|---|---|---|
| Toothpaste A | Sorbitol + Glycerin | None | 0.077 | 0.005 | 93.5 | 0.0025 | 96.7 |
| Toothpaste B | Sorbitol | None | 0.114 | 0.072 | 36.8 | 0.049 | 57.0 |
| Toothpaste C | None | Sodium lauroyl sarcosinate | 0.12 | 0.11 | 8.3 | 0.10 | 16.6 |
| Toothpaste E | None | Sodium cocoyl sarcosinate | 0.14 | 0.14 | 0 | 0.13 | 9.3 |
| Toothpaste F | None | Sodium myristoyl sarcosinate | 0.13 | 0.13 | 0 | 0.14 | 0 |

TABLE 4-continued

Comparison of stability of Toothpastes prepared with different N-acyl sarcosinate compounds at 40° ± 1° C. and 70-75% RH

| | | | Initial | 2 Month | | 3 Month | |
|---|---|---|---|---|---|---|---|
| Composition | Humectant | N-Acyl Sarcosinate | SCD* (%) | SCD (%) | Loss (%) | SCD (%) | Loss (%) |
| Toothpaste G | Sorbitol | Sodium lauroyl sarcosinate | 0.14 | 0.13 | 7.3 | 0.13 | 9.5 |
| Toothpaste H | None | None | 0.13 | 0.13 | 0 | 0.13 | 9.5 |

*SCD: Stabilized chlorine dioxide

Toothpastes C, E and F containing sodium lauroyl sarcosinate, sodium cocoyl sarcosinate sodium myristoyl sarcosinate exhibited 16.6%, 9.3% and 0% loss in the stabilized chlorine dioxide after 3 months at 40±1° C. and 70-75% RH, respectively. As discussed earlier, the stability for 3 months at 40±1° C. and 70-75% RH corresponds to 1 year of shelf life at room temperature. The loss of stabilized chlorine dioxide in 3 months at 40±1° C. and 70-75% RH for toothpastes A and B prepared following teachings of prior art was 96.7% and 57.0%, respectively. Measurement variability in estimation of chlorine dioxide by titration method is about 10%. Therefore, any loss >10% is considered as observed loss. The results demonstrate that N-acyl sarcosinate compounds significantly enhanced the stability of stabilized chlorine dioxide. Toothpaste G that contains both sorbitol and sodium lauroyl sarcosinate exhibited 9.5% loss in stabilized chlorine dioxide in 3 months at 40±1° C. and 70-75% RH. Similarly, Toothpaste H that does not contain sorbitol exhibited 9.5% loss in stabilized chlorine dioxide in 3 months at 40±1° C. and 70-75% RH. The results confirm prior art that polyhydroxy compounds such as sorbitol and glycerin react with chlorite salts thereby resulting in unstable compositions.

In addition to the stability of stabilized chlorine dioxide consumer goodness properties such as flavor, taste, and consistency of the toothpaste are important for preparing a marketable composition. Viscosity of the toothpaste preparations was determined using Spindle 1 at 30 rpm. The results are summarized in Table 5.

TABLE 5

Viscosity of toothpaste preparations

| Composition | Viscosity (Spindle 1 at 30 rpm) |
|---|---|
| Toothpaste A | 1531 cp |
| Toothpaste B | 1538 cp |
| Toothpaste C | 1544 cp |
| Toothpaste E | 1625 cp |
| Toothpaste F | 1263 cp |
| Toothpaste G | 2306 cp |
| Toothpaste H | 713 cp |

The viscosity data in Table 5 demonstrate significant differences for Toothpastes A-H. Viscosity of Toothpaste H was significantly lower (713 cp) compared to other toothpaste preparations, particularly Toothpastes A through F (range 1263 cp-1625 cp). Further, Toothpaste H did not form a uniform ribbon of toothpaste and did not hold or rest very well on a toothbrush. Such preparation does not meet the consumer goodness characteristics for a consumer product. On the other hand, viscosity of Toothpaste G was significantly higher (2306 cp) compared to other toothpaste preparations, particularly Toothpastes A through F (range 1263 cp-1625 cp). Toothpaste G was hard to squeeze out from the tubes at its viscosity and did not form a uniform ribbon. Accordingly, this level of viscosity renders it unsuitable as toothpaste. Thus, Toothpastes C, D, E and F exemplify the stability, shelf-life and viscosity characteristics of a desired toothpaste embodiment.

Example 4: Enamel Fluoride Uptake and Remineralization and Demineralization

The following study was performed to determine the efficacy of an embodiment to (a) promote enamel fluoride uptake and (b) promote lesion remineralization under dynamic conditions simulating in vivo caries formation. The model and methods used are described in the literature (White 1987, 1988; Schemehorn et. al. 1990, 1992, 1994).

Test Products: US Pharmacopoeia Reference Standard for fluoride toothpaste i.e. Fluoride Dentifrice: Sodium Fluoride/Silica, Catalog No. 127752 was procured from US Pharmacopoeia store, 12601 Twinbrook Parkway, Rockville, Md. 20852-1790. Crest 3D White Mild Mint and Colgate Total Advanced Whitening Toothpaste were purchased from a local store. Toothpaste B was prepared following the teachings of U.S. Patent Application U.S. 2011/0318282. Toothpaste C was prepared following the teaching as described herein and according to Exemplary Composition I.

Specimen Preparation: Enamel specimens (3 mm diameter) were removed from extracted bovine teeth and mounted in rods. The specimens were ground and polished to a high luster with Gamma Alumina using standard methods. Eighteen specimens per group were prepared for this study.

Initial Decalcification: Artificial lesions were formed in the enamel specimens by a 33-hour immersion into a solution of 0.1 M lactic acid and 0.2% Carbopol C907 which was 50% saturated with hydroxyapatite and adjusted to pH 5.0. The lesion surface hardness range was 25-45 Vickers microhardness (VHN; 200 gF, 15 s dwell time) and average lesion depth was approximately 70 μm.

Remineralizing Solution: Pooled Human Saliva (collected fresh from multiple donors, pooled and kept frozen until time of use) was used as the remineralizing solution. Fifteen (15) ml of remineralizing solution was placed into color codes 30 ml treatment beakers. Fresh saliva was used each day (changed during the acid challenge period).

Treatment Slurries: During the treatment period, the specimens were immersed in dentifrice slurries to simulate daily brushing. The slurries were prepared by adding 5.0 g of Toothpaste B or Toothpaste C to 10 g of deionized water in a beaker with a magnetic stirrer. Fresh slurries were prepared for each of the two carriers just prior to each treatment.

Treatment Regimen: The cyclic treatment regimen consisted of a 4.0 hour/day acid challenge in the lesion forming solution described above with four, one-minute dentifrice treatment periods. After the treatments, the specimens were rinsed with running distilled water and then replaced back into the human saliva. The remaining time (~20 hours) the specimens were in the human saliva. The regimen was repeated for 10 days and interim Surface Micro-Hardness (SMH) measurements were obtained. The specimens were then subject to an additional 10 days of the treatment regimen for a total of 20 days. The treatment schedule used for this experiment was as follows (on the first day, Step 1 was not given; the test began with one hour in human saliva to permit pellicle development prior to any treatments):

| Step 1:- | 8:00 a.m.-8:01 a.m. | Dentifrice treatment |
| Step 2:- | 8:01 a.m.-9:00 a.m. | Remineralizing treatment |
| Step 3:- | 9:00 a.m.-9:01 a.m. | Dentifrice treatment |
| Step 4:- | 9:01 a.m.-10:00 a.m. | Remineralizing treatment |
| Step 5:- | 10:00 a.m.-2:00 p.m. | Acid challenge |
| Step 6:- | 2:00 p.m.-3:00 p.m. | Remineralizing treatment |
| Step 7:- | 3:00 p.m.-3:01 p.m. | Dentifrice treatment |
| Step 8:- | 3:01 p.m.-4:00 p.m. | Remineralizing treatment |
| Step 9:- | 4:00 p.m.-4:01 p.m. | Dentifrice treatment |
| Step 10:- | 4:01 p.m.-8:00 a.m. | Remineralizing treatment |
| Step 11:- | Back to Step 1 | |

Fluoride Analysis: At the end of the 20-day treatment regimen, the fluoride content of each enamel specimen was determined using the micro-drill technique to a depth of 100 μm. Fluoride data were calculated as μg F/cm$^3$ (μg F×dilution factor/volume of drilling).

Remineralization Measurements: Both 10-day and 20-day Surface Micro Hardness (SMH) assessments were conducted. The difference between the hardness following treatment and initial lesion hardness indicated the ability of that treatment to enhance remineralization.

Figure 2:
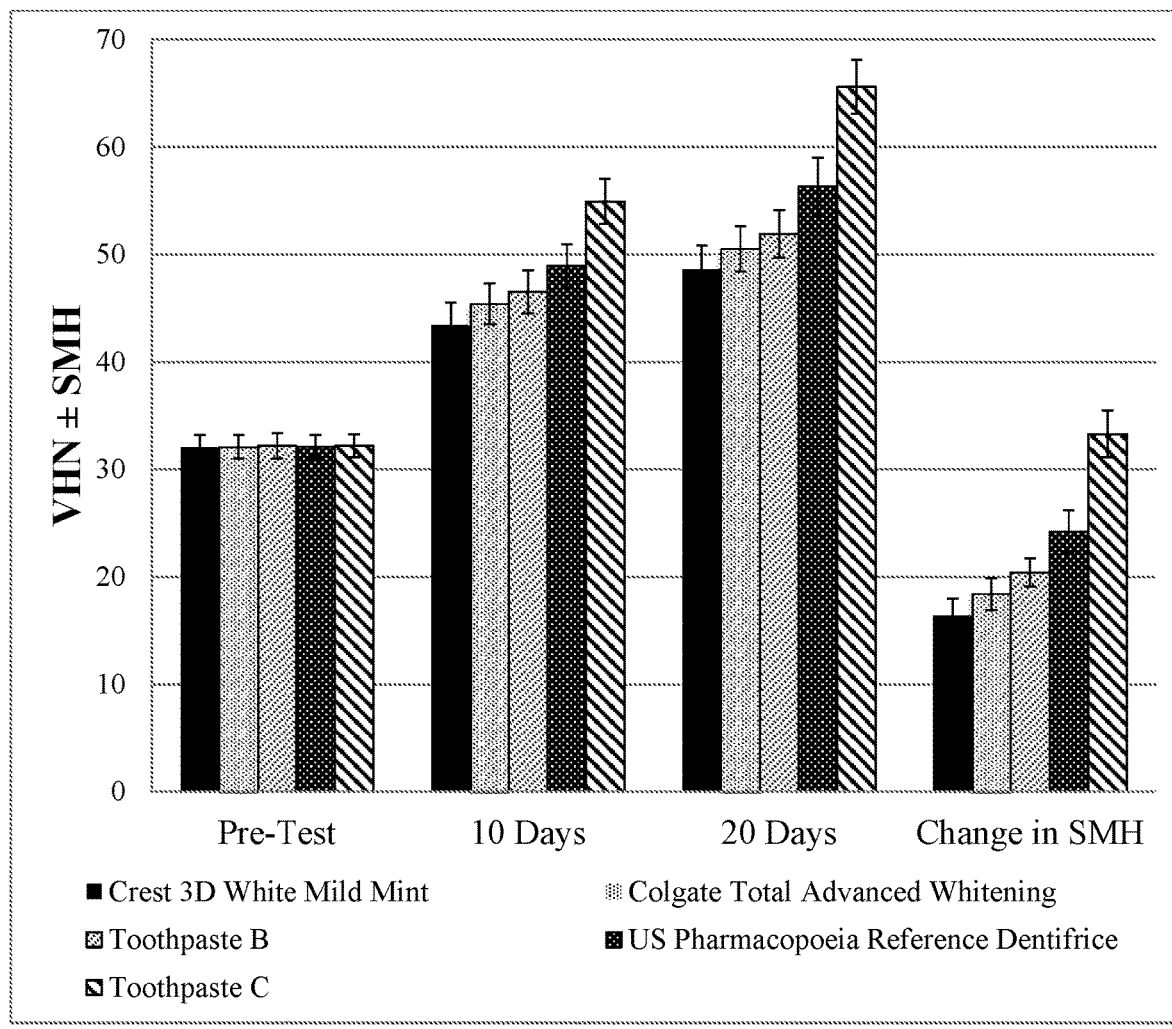
FIG. 2 is a graph illustrating tooth remineralization of commercial products to an oral care composition according to an embodiment.

Results: The fluoride uptake data is summarized in Table 6 and FIG. 1 and the summary of surface hardness changes representing remineralization is presented in Table 7 and FIG. 2. Statistical analyses were performed with a one-way analysis of variance model using Sigma Plot Software (13.0). Since significant differences were indicated, the individual means were analyzed by the Student Newman Keuls (SNK) test.

TABLE 6

Incipient Lesion Fluoride Uptake

| | Fluoride Uptake (μg F/cm$^3$) | |
| --- | --- | --- |
| Toothpaste | Mean (n = 18) | SEM |
| Crest 3D White Mild Mint | 1389 | ±64 |
| Colgate Total Advanced Whitening | 2697 | ±174 |
| US Pharmacopoeia Reference Dentifrice | 2857 | ±187 |
| Toothpaste B | 3451 | ±202 |
| Toothpaste C | 5603 | ±365 |

Toothpaste C exhibited 62.3% more fluoride uptake into incipient lesioned enamel compared to Toothpaste B of U.S. Patent Application U.S. 2011/0318282 (Table 6). Also, the fluoride uptake by Toothpaste C was 96.1%, 107.7%, and 303.3% higher than US Pharmacopoeia Reference Dentifrice, Colgate Total Advanced Whitening, and Crest 3D White Mild Mint toothpastes, respectively (Table 6). Combined effect of sodium lauroyl sarcosinate and stabilized chlorine dioxide in enhancing fluoride uptake in tooth enamel by Toothpaste C compared to Toothpaste B of prior art, US Pharmacopoeia Reference Material, and commercial products is an unexpected result.

TABLE 7

Surface Micro Hardness after 10 and 20 days of remineralization treatment

| | Surface Micro Hardness (SMH) | | | | |
| --- | --- | --- | --- | --- | --- |
| | Baseline | After 10 Days | | After 20 Days | |
| Toothpaste | (Pre-Test) SMH | SMH | Change in SMH | SMH | Change in SMH |
| Crest 3D White Mild Mint | 32.1 | 43.4 | 11.3 | 48.6 | 16.4 |
| Colgate Total Advanced Whitening | 32.1 | 45.4 | 13.3 | 50.5 | 18.4 |
| Toothpaste B | 32.2 | 46.5 | 15.0 | 51.9 | 20.4 |
| US Pharmacopoeia Reference Dentifrice | 32.1 | 48.9 | 16.8 | 56.3 | 24.2 |
| Toothpaste C | 32.2 | 54.9 | 22.6 | 65.6 | 33.3 |

The protocol for the remineralization study involved repeated acid challenge and remineralization treatment. Therefore, net increased in Surface Micro-Hardness is combined result of enhanced remineralization and reduced demineralization. Toothpaste C exhibited 63.2% more remineralization after 20 days compared to Toothpaste B of U.S. Patent Application U.S. 2011/0318282 (Table 7). Also, the remineralization after 20 days by Toothpaste C was 37.6%, 80.9%, and 103.0% higher than US Pharmacopoeia Reference Dentifrice, Colgate Total Advanced Whitening, and Crest 3D White Mild Mint toothpastes, respectively. The remineralization results at 10 days and 20 days intervals were consistent further confirming increased remineralization (Table 7). An unexpected discovery from this study is the combined effect of sodium lauroyl sarcosinate and stabilized chlorine dioxide in a multi-component composition increased remineralization (combined result of enhanced remineralization and reduced demineralization) as shown by the enhanced fluoride uptake by Toothpaste C when compared to Toothpaste B of prior art, US Pharmacopoeia Reference Material, and the selected fluoride toothpaste commercial products.

Example 5: Pellicle Cleaning and Plaque Removal Study

The study below was performed to determine the plaque removal capability of an embodiment as determined by removal of stained pellicle. The method used was developed in order to assess the ability of dentifrices to remove stained pellicle, i.e., to determine the cleaning ability of complete dentifrice formulations. Published studies demonstrate that the results of this test method with dentifrice slurries were comparable to those obtained in controlled clinical trials (Stookey et al. 1982). Thus, this methodology is routinely used in the development of more effective cleaning dentifrice formulations.

Test Product: Toothpaste B was prepared following the teachings of U.S. Patent Application U.S. 2011/0318282. Toothpaste C was prepared following the teaching as described herein. The American Dental Association (ADA) reference material was procured from Odontex Inc., Lawrence, Kans., USA.

Specimen Preparation: Bovine, permanent, central incisors were cut to obtain labial enamel specimens approximately 10×10 mm. The enamel specimens were embedded in an autopolymerizing methacrylate resin so that only the enamel surfaces were exposed. The enamel surfaces were then smoothed and polished on a lapidary wheel and lightly etched to expedite stain accumulation and adherence. They were placed on a rotating rod (~37° C. incubator), which alternately exposed them to air and to a solution having PGY broth, tea, coffee, mucin, $FeCl_3$, and *Micrococcus luteus*. The staining broth was changed and specimens were rinsed daily until a uniform stain had accumulated. After approximately seven days, a darkly stained pellicle film was apparent on the enamel surfaces. Specimens were rinsed, allowed to air dry, and refrigerated until used. All products were tested using specimens prepared at the same time.

Scoring and Set-Up: The amount of in vitro stain was graded photometrically using only the L value of the L*a*b* scale using a spectrophotometer (Minolta CM2600d). The area of the specimens scored was a ¼-inch diameter circle in the center of the 10×10 mm enamel. Specimens with scores between 30 and 42 (30 being more darkly stained) were used. On the basis of these scores, the specimens were divided into groups with each group having approximately the same average baseline score.

Procedure: The specimens were mounted on a mechanical V-8 cross-brushing machine equipped with soft nylon-filament (Oral-B 40) toothbrushes. Tension on the enamel surface was adjusted to 150 g. The dentifrices were tested as slurries prepared by mixing 25 grams of dentifrice with 40 ml of deionized water. The American Dental Association (ADA) Reference Material was the ADA abrasion standard (10 g/50 ml of a 0.5% CMC solution). The specimens were brushed for 800 strokes (4.5 minutes). To minimize mechanical variables, ten specimens per group were brushed on each of the eight brushing heads. Different test products were used on each run, with one tube of slurry made up for each product. Fresh slurry was made after being used to brush four specimens. Following brushing, specimens were rinsed, blotted dry, and scored again for stain, as previously described.

Calculations: The difference between the pre- and post-brushing stain scores was determined and the mean and standard error of measurement (SEM) was calculated for the reference group in each study. The mean decrement between the pre- and post-brushing stain scores was determined for the ADA Reference Material group, and assigned a pellicle cleaning ratio (PCR) value of 100. A constant value was calculated by dividing the mean decrement of the ADA Reference Material into 100. The individual PCR value for each specimen was calculated by multiplying its individual decrement by the calculated constant.

The mean, standard deviation and SEM for each test group were then calculated using the individual PCR values. The larger the PCR value, the greater the amount of stained pellicle removed from the enamel surface in this test. Data exhibiting outlier values was not considered for calculating pellicle cleaning ratio. The mean and SEM for each group was then calculated using the individual cleaning ratios. Data was analyzed using a one-way analysis of variance model (IBM SPSS Statistics 24 Software). Data was further analyzed doing all pairwise multiple comparison procedures (Student-Newman-Keuls method). All analyses were done with the significance level set at 0.05.

Results: Initially, the studies were conducted with 15 replicates (n=15) of each sample.

The mean pellicle cleaning ratio of Toothpaste B, Toothpaste C, and ADA Reference Material were 95.9, 101.21, and 100.0, respectively. Further, the SEM around the mean was +2.46, +2.83, and +2.85, respectively. Therefore, Toothpaste C was most effective in removing removal of stained pellicle followed by to ADA reference material and Toothpaste B. It is important to note that Toothpaste C exhibited 5.5% higher mean pellicle cleaning ratio on numerical basis compared to Toothpaste B. However, the difference was not statistically significant since the p value for the difference between the SEM around the mean for groups was >0.05. Because the testing was conducted with the routine number of replicates, the novel discovery of the current invention was not disclosed through routine testing protocol.

The inventors repeated studies using 80 replicates (n=80) to provide a sufficiently robust number of replicates to account for the variability associated with the standard error of measurement (SEM) and allow the outcomes of the discovery to be revealed as statistically significant. The results are summarized in the Table 8.

TABLE 8

Pellicle Cleaning Ratio of Dentifrices

| Toothpaste | n | Pellicle Cleaning Ratio | |
|---|---|---|---|
| | | Mean | SEM |
| Toothpaste B | 76 | 94.48 | ±1.12 |
| ADA Reference Material | 75 | 100.00 | ±1.20 |
| Toothpaste C | 75 | 103.51 | ±0.96 |

The observation that Toothpaste C was most effective in removal of stained pellicle compared to ADA reference material and Toothpaste B was affirmed with the higher number of replicates. Further, Toothpaste B was less effective in removal of stained pellicle compared to ADA reference material. Importantly, the p-value for the difference between the groups was <0.05. Therefore, removal of stained pellicle Toothpaste C compared to Toothpaste B of U.S. Patent Application U.S. 2011/0318282 and ADA Reference Material was statistically significant. Combined effect of sodium lauroyl sarcosinate and stabilized chlorine dioxide in enhancing removal of stained pellicle that corresponds to plaque removal from tooth enamel by Toothpaste C compared to Toothpaste B of prior art and ADA Reference Material is an unexpected result. The results demonstrate that the results of Toothpaste C were unexpected over the prior art.

Example 6: Regrowth of Oral Polymicrobial Biofilm

The following study was performed to determine the effect of an embodiment on preventing 24 hours regrowth of oral polymicrobial biofilm containing a mixed salivary bacterial preparation on bovine enamel surfaces.

Test Product: Toothpaste C was Prepared Following the Teaching as Described Herein.

Experimental Design: 4×4 mm bovine enamel sections (embedded in 12×12×7 mm acrylic resin) were prepared for use in sterile 12 well tissue culture plates and sterilized by ethylene oxide (EtO). Three ml of Brain Heart Infusion broth supplemented with Yeast Extract and Vitamin K and hemin (BHI-YE) was inoculated with 50 µl of an overnight culture of a mixed species whole salivary bacterial preparation in the wells of the tissue culture plate containing the sections (1 section/well). The plates were incubated for 24 hours to grow the biofilm on the enamel. In order to remove the biofilm similar to a human subject brushing his/her teeth the sections were brushed with Toothpaste C (3 sections/paste) for a brushing schedule similar to a 30 second brushing by human subjects. The sections were rinsed with sterile water and inserted into a fresh tissue culture plate containing 3 ml of BHI-YE to facilitate regrowth of the remaining oral biofilm on the enamel sections. The plates were incubated for 24 hours. The sections were removed, placed in 2 ml of sterile saline, sonicated for 10 sec, vortexed for 10 sec, diluted to 1:10 and 1:1000 and spiral plated on blood agar plates. After 24 hours of incubation, the colonies on the agar plates were counted using an automated colony counter. The methods are described in published literature (Huang et al. 2012 and Sabrah et al. 2015).

Results: The results of the biofilm viability (CFU/ml) assay are presented in Table 9.

TABLE 9

Regrowth of Oral Polymicrobial Biofilm

| Sample number | Mean CFU/ml | Group Mean CFU/ml | p value compared to Control |
|---|---|---|---|
| Toothpaste C-1 | $1.04 \times 10^7$ | $5.08 \times 10^7$ | 0.018 |
| Toothpaste C-2 | $1.39 \times 10^8$ | | |
| Toothpaste C-3 | $3.18 \times 10^6$ | | |
| Control-1 | $8.31 \times 10^7$ | $13.1 \times 10^7$ | NA |
| Control-2 | $9.96 \times 10^7$ | | |
| Control-3 | $2.09 \times 10^8$ | | |

There was a significant reduction in regrowth of oral polymicrobial biofilm obtained by Toothpaste C compared to the water brushed control (p<0.05). Regrowth of oral polymicrobial biofilm is directly proportional to quantity of residual bacteria after brushing. Therefore, the results demonstrate the Toothpaste C is highly effective killing bacteria in oral polymicrobial biofilm.

Example 7: Spectrometric Analysis of the Embodiments

The following study was performed to determine the quantity of chlorite ion available in an embodiment of the present disclosure. Such available quantity of chlorite ion and not the stabilized chlorine dioxide is important for reaction with the salivary biomolecules in the oral cavity. The methodology used was standard UV-visible spectrometry.

Test Products: Toothpaste B was prepared following the teachings of U.S. Patent Application U.S. 2011/0318282. Toothpaste C was prepared following the teaching as described herein. Sodium chlorite was purchased from Sigma-Aldrich, 3050 Spruce St., St. Louis, Mo. 63103.

Specimen Preparation: 0.02 mM phosphate buffer pH 7.0 was prepared using HPLC grade water. 200 mg of toothpaste A and toothpaste B was suspended in 3.0 ml of 0.02 mM phosphate buffer pH 7.0 and homogenized thoroughly using rotamix. The homogenous mixture was then centrifuged at 3,500 rpm for 30 minutes. Clear supernatant was collected. Aqueous toothpaste extracts were used for spectrophotometric analysis. Each toothpaste product was processed in 5 replicates. pH adjusted HPLC-grade water served as a suitable control for recording the spectra.

Recording of Spectra: Zero-order electronic absorption spectra of aqueous extracts of toothpaste products and aqueous authentic sodium chlorite ($Na^+/ClO_2^-$) solution were recorded on a PC-controlled Jasco V730 UV-visible spectrophotometer at a pH value of 7.0 (scan rate 120 nm/min). From the extinction coefficient (ε) values of $ClO_2^-$ and $OCl^-$ (at max values of 262 and 292 nm, respectively), multivariate spectral curve resolution analysis of datasets consisting of a range of oral dilutions were subjected to multivariate curve resolution (MCR) analysis for determining the concentration of chlorite ion ($ClO_2^-$; predominant active agent).

Figure 3:
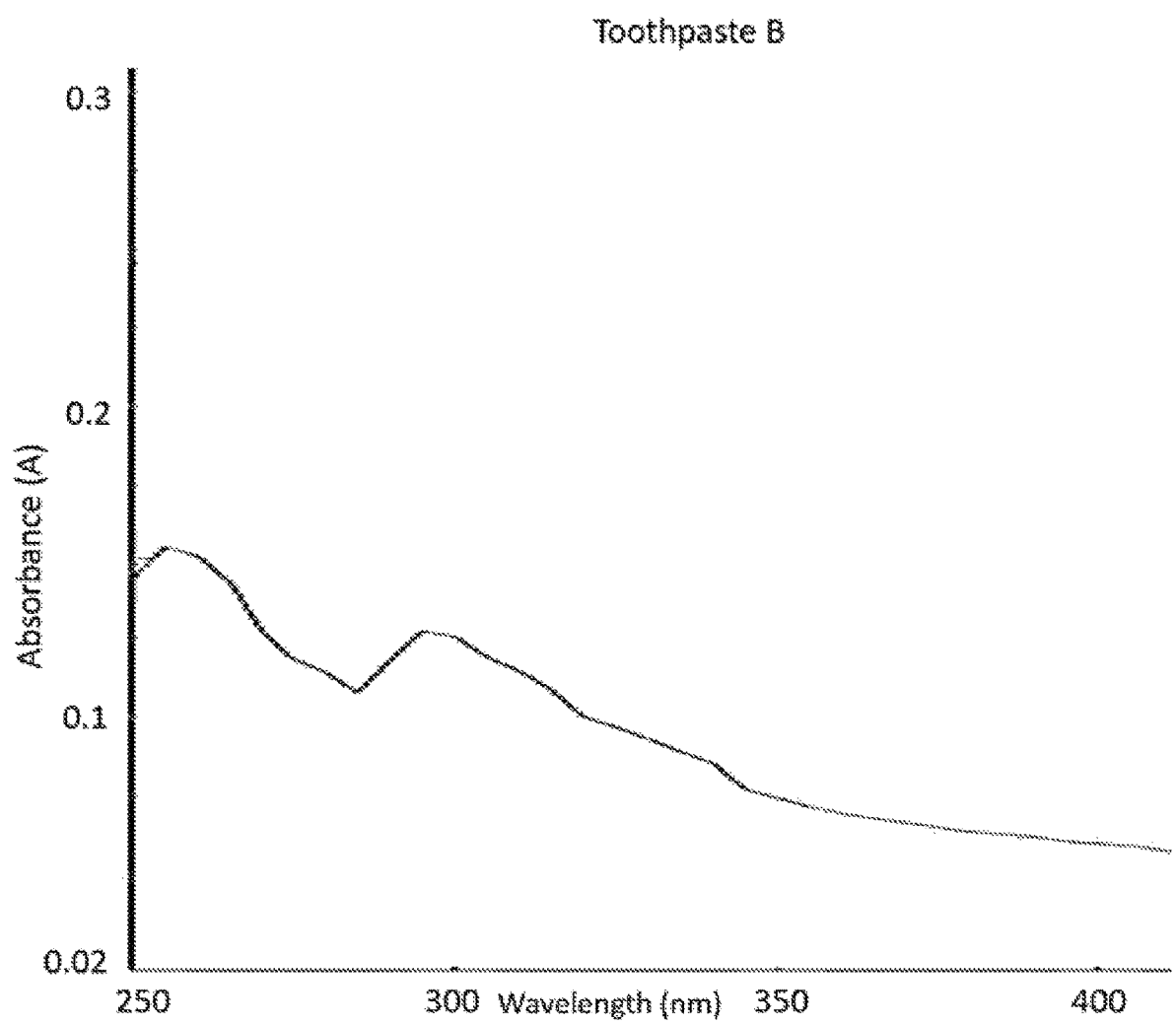
FIG. 3 illustrates zero-order electronic absorption spectra of aqueous extracts of Toothpaste B.
Figure 4:
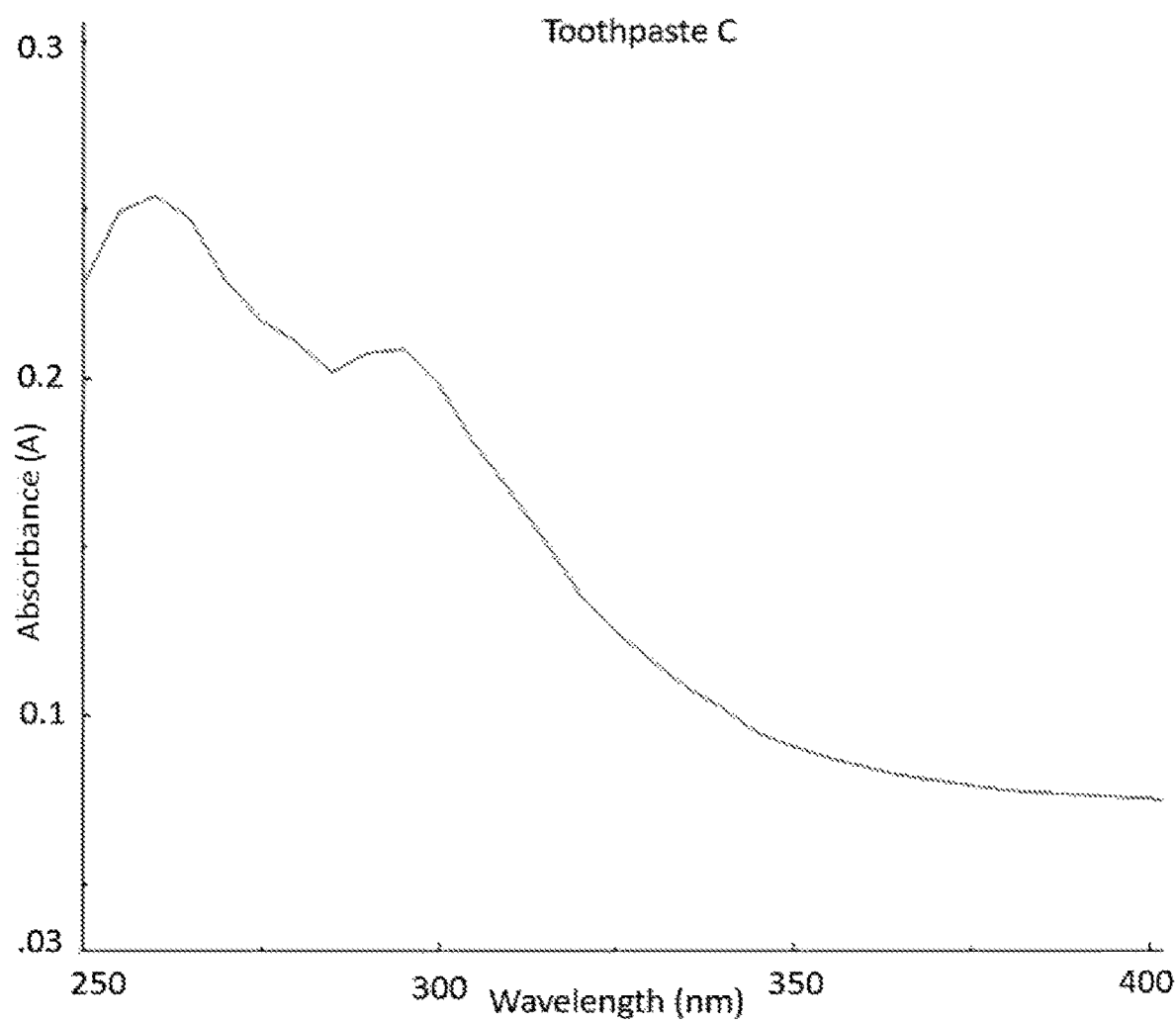
FIG. 4 illustrates zero-order electronic absorption spectra of aqueous extracts of Toothpaste C.

Results: Electronic absorption spectra of Toothpaste B and Toothpaste C are presented in FIG. 3 and FIG. 4, respectively.

Both Toothpaste B and Toothpaste C showed two clear absorption bands located at 262 nm and 295 nm. Absorption peak at 262 nm corresponds to active chlorite anion and the peak at 295 nm is attributed to hypochlorite anion generated from the decomposition of chlorite, and/or chemical reaction of chlorite with other ingredient in the toothpaste. Absorbance peak of chlorite ion ($ClO_2^-$) at 262 nm of Toothpaste B was 0.155 and that for Toothpaste C was 0.255. Higher absorbance in Toothpaste C demonstrates 64.5% higher quantity of available chlorite ion ($ClO_2^-$) compared to Toothpaste B. Such higher quantity of available chlorite ion by Toothpaste C compared to Toothpaste B of prior art is an unexpected result. The results demonstrate that the results of Toothpaste C were unexpected over the prior art. Not to be bound by any particular theory, a benefit of having 64.5% more available chlorite ion is that it is available for its increased effect in the oral cavity. This result of the use of compositions as taught by this embodiment is further proved by oxidation of salivary biomolecules such as pyruvate and L-methionine as described in Example 8.

Example 8: Oxidation of Salivary Biomolecules by $^1$H NMR Analysis

The following study was performed to determine the efficacy of an embodiment of the present disclosure for oxidation of biomolecules in saliva. Oxidation of pyruvate to acetate and L-methionine to methionine sulfoxide was monitored by $^1$H NMR spectroscopy.

Test Products: Toothpaste B was prepared following the teachings of U.S. Patent Application U.S. 2011/0318282. Toothpaste C was prepared following the teaching as described herein.

Aqueous Toothpaste Extract Preparation: 0.02 mM phosphate buffer pH 7.0 was prepared using HPLC grade water. 200 mg of Toothpaste B and Toothpaste C was suspended in 3.0 ml of 0.02 mM phosphate buffer pH 7.0 and homogenized thoroughly using rotamix. The homogenous mixture was then centrifuged at 3,500 rpm for 30 minutes. Clear supernatant was collected. Aqueous toothpaste extracts thus prepared was used for the study.

Human Saliva Sample Preparation: 0.6 ml of aqueous extract of the toothpaste composition to be tested was mixed with 0.6 ml of aliquots of each salivary supernatant sample collected from healthy volunteers (n=10). After thorough rotamixing, these mixtures were equilibrated at a temperature of 35° C. for 30 and 60 second periods, and then stored at −80° C. for a maximal duration of 72 hours prior to $^1$H NMR analysis. 0.6 ml aliquots of each salivary supernatant sample mixed with 0.6 ml of HPLC-grade water (previously thoroughly sparged with Helium gas for a 30 min. period) in place of the extracts of toothpaste products and then also equilibrated and stored in the same manner served as essential controls.

Time Dependent Oxidation of Pyruvate to Acetate and Methionine to Methionine Sulfoxide: Aqueous solutions containing 0.02 mM of sodium pyruvate and L-methionine were prepared in 0.05 mM phosphate buffer (pH 7.0) and rigorously deoxygenated via purging with Helium gas for 30 mins at ambient temperature prior to use. 1.00 ml aliquots of this solution were individually treated with equivalent volumes of aqueous extract of the toothpaste composition. The mixture was then equilibrated at a temperature of 35° C. for 30 and 60 seconds and stored at −80° C. for a maximal period of 72 hours prior to the acquisition of $^1$H NMR spectra. 1.0 ml aliquots of sodium pyruvate or L-methionine solution treated with an equivalent volume of HPLC-grade water equilibrated and stored in the same manner served as respective control.

$^1$H NMR Measurements: A 0.60 ml aliquot of sample prepared as described above was placed in 5-mm diameter NMR tubes and 0.1 ml of a 0.00225 mM solution of sodium 3-trimethylsilyl-(2,2,3,3-2H4)-1-propionate [TSP, internal chemical shift reference and quantitative $^1$H NMR internal standard (δ=0.00 ppm)] in deuterium oxide ($^2$H$_2$O) was added, the latter to provide a field frequency lock. Single-pulse and/or Carr-Purcell-Meiboom-Gill (CPMG) spin-echo $^1$H NMR spectra was acquired on a Bruker Avance AV-400 spectrometer at an operating frequency of 399.94 MHz and a probe temperature of 293 K. The one-dimensional (1D) NOESY pulse sequence with presaturation of the biofluid water signal were employed throughout. Chemical shift values were referenced to the added TSP for these samples, together with the —CH$_3$ group signals of selected biomolecules detectable. All $^1$H NMR spectra were acquired in duplicate, a random order and an automated manner using a sample changer for continuous sample delivery. Two-dimensional (2D) shift-correlated $^1$H-$^1$H spectra of biofluid samples were also acquired.

Results: $^1$H NMR-linked metabolomics analysis of human salivary sample supernatants revealed that aqueous extracts from Toothpaste C formulation was reproducibly more effective than those from Toothpaste B in oxidation of pyruvate to acetate and methionine to methionine sulfoxide. The observation was further confirmed by a time dependent study wherein solutions of sodium pyruvate and methionine were treated with aqueous extracts of Toothpaste B and Toothpaste C each for 30 and 60 seconds. The results are summarized in Table 10.

TABLE 10

Oxidation of Salivary Biomolecules as Determined by $^1$H NMR Study

| Time | Oxidation of Sodium Pyruvate [Acetate]:[Pyruvate] Ratio | | Oxidation of L-Methionine [Methionine Sulfoxide]:[Methionine] | |
|---|---|---|---|---|
| | Toothpaste B | Toothpaste C | Toothpaste B | Toothpaste C |
| 0 Seconds | $0.149 \times 10^{-3}$ | $0.149 \times 10^{-3}$ | $1.58 \times 10^{-3}$ | $1.69 \times 10^{-3}$ |
| 30 Seconds | $1.30 \times 10^{-3}$ | $9.57 \times 10^{-3}$ | $5.55 \times 10^{-3}$ | $13.0 \times 10^{-3}$ |
| 60 Seconds | $3.08 \times 10^{-3}$ | $11.30 \times 10^{-3}$ | $5.75 \times 10^{-3}$ | $14.0 \times 10^{-3}$ |

The ratio of concentrations of acetate:pyruvate within 30 and 60 seconds of interaction with Toothpaste C was 7.36 and 3.66 fold higher compared to Toothpaste B, respectively. Similarly, The ratio of concentrations of methionine sulfoxide:methionine within 30 and 60 seconds of interaction with Toothpaste C was 2.34 and 2.43 fold higher compared to Toothpaste B, respectively. The results demonstrate that Toothpaste C oxidized salivary biomolecules at much faster rate and in greater quantity compared to Toothpaste B.

Lower oxidizing activity of Toothpaste B is attributed to the partial consumption of stabilized chlorine dioxide by sorbitol present in it. The results are also aligned with the lower stability of stabilized chlorine dioxide of Toothpaste B (as presented in Table 3). Combined effect of sodium lauroyl sarcosinate and stabilized chlorine dioxide in enhancing the oxidation of salivary biomolecules by Toothpaste C compared to Toothpaste B of prior art is an unexpected result. The results demonstrate that Toothpaste C was more effective at oxidizing sodium pyruvate and L-methionine over the prior art. Not to be bound by a particular theory, the increased levels of sodium chlorite seen in Example 7 may have led to the increased oxidation reaction. Though this is true, this is not the only factor that can contribute to the oxidation reaction. Physcio-chemical properties of other components in the embodiments may also contribute. For example, sorbitol is known to react with chlorine dioxide. Therefore, the oxidation reaction is less in Toothpaste B. In contrast, available chlorine dioxide in Toothpaste C reacts with only salivary biomolecules (in absence of sorbitol in the composition). Further, altered microenvironment of hydrophilicity due to an N-acyl sarcosinate may also contribute to higher oxidation reaction.

Each of the exemplary compositions and those against which they were compared were suitable for use as a prophylactic treatment for cleaning the teeth, by applying the composition formulated as a paste to the tooth surface when disposed in a tube as employed by individuals in routine home oral hygiene procedures of tooth brushing.

The detailed description shows embodiments by way of illustration, including the best mode. While these embodiments are described in sufficient detail to enable those skilled in the art to practice the principles of the present disclosure, it should be understood that other embodiments may be realized and that chemical changes may be made without departing from the spirit and scope of principles of the present disclosure. Thus, the detailed description herein is presented for purposes of illustration only and not of limitation. With regard to procedures, methods, techniques, and workflows that are in accordance with some embodiments, some operations in the procedures, methods, techniques, and workflows disclosed herein may be combined and/or the order of some operations may be changed. For example, the steps recited in any of the method descriptions may be executed in any suitable order and are not limited to the order presented.

In the above description, all cited references are incorporated herein by reference in their entireties. The citing of any reference is not an admission that such a reference is relevant prior art; rather, citations are to reference the novelty of the invention and discoveries described herein relative to known scientific literature, practices and prior art. In the description of the Present Invention, all ratios are weight ratios unless specifically stated otherwise. Unless otherwise indicated or evident from context, preferences indicated above and herein apply to the entirety of the embodiments discussed herein.

In describing the present disclosure, the following terminology will be used: The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3 and 4 and sub-ranges such as 1-3, 2-4 and 3-5, etc.

This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

The scope should be determined by the appended claims and their legal equivalents, rather than by the examples given above. For example, the operations recited in any method claims may be executed in any order and are not limited to the order presented in the claims. Moreover, no element is essential unless specifically described herein as "critical" or "essential."

Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

The invention claimed is:

1. A single phase composition comprising:
   from about 0.01% to about 5.0% of an aliphatic anionic compound, based on a total weight of the single phase composition;
   from about 0.001 to about 8.0% of an oxidative compound, based on a total weight of the single phase composition;
   a buffering system, wherein pH of the single phase composition is between 6.0 and 8.0; and
   water, wherein the aliphatic anionic compound provides enhanced stability for the oxidative compound,
   wherein the oxidative compound is sodium chlorite,
   wherein the buffering system comprises disodium hydrogen phosphate and sodium dihydrogen phosphate,
   wherein the aliphatic anionic compound is an N-acyl sarcosinate, wherein the N-acyl sarcosinate is at least one of sodium lauroyl sarcosinate, sodium cocoyl sarcosinate, sodium myristoyl sarcosinate, sodium oleoyl sarcosinate, or sodium stearoyl sarcosinate,
   wherein the single phase composition exhibits less than 35% loss of the oxidative compound for a period of 24 months at about 25° C.

2. The single phase composition of claim 1, wherein the single phase composition is formulated into a form of, at least one of, a mouth rinse, a gum, a gel, a paste, a cream, spray, and a lozenge.

3. The single phase composition of claim 1, further comprising an orally acceptable aqueous vehicle comprising at least one of a humectant, an abrasive, a pharmaceutically acceptable carrier, a fluoride ion source, and a thickening agent.

4. The single phase composition of claim 1, wherein the single phase composition oxidizes salivary biomolecules.

5. The single phase composition of claim 4, wherein the single phase composition oxidizes salivary biomolecules in 30 to 120 seconds of contact with saliva.

6. The single phase composition of claim 5, wherein the salivary biomolecules are pyruvate and L-methionine.

7. The single phase composition of claim 1, wherein the single phase composition is applied to, at least one of, anal, aural, nasal, oral, and urogenital cavities.

8. A single phase composition comprising:
   from 0.01% to 2.5% sodium lauroyl sarcosinate, based on a total weight of the single phase composition;
   from 0.01% to 0.014% of oxidative compound, based on a total weight of the single phase composition;
   a buffering system comprising disodium hydrogen phosphate and sodium dihydrogen phosphate collectively at up to about 2.4% based on a total weight of the single phase, wherein pH of the single phase composition is between 6.0 and 8.0; and
   at least 64% water based on a total weight of the single phase composition;
   wherein the oxidative compound is sodium chlorite; and
   wherein the single phase composition exhibits less than 35% loss of the oxidative compound for a period of 24 months at about 25° C.

9. The single phase composition of claim 8, comprising 2.5% of the sodium lauroyl sarcosinate, based on a total weight of the single phase composition, and 0.14% of the oxidative compound, based on a total weight of the single phase composition.

10. A single phase composition comprising:
    from 0.01% to 2.5% sodium myristoyl sarcosinate, based on a total weight of the single phase composition;
    from 0.01% to 0.14% of oxidative compound, based on a total weight of the single phase composition;
    a buffering system comprising disodium hydrogen phosphate and sodium dihydrogen phosphate collectively at up to about 2.4% based on a total weight of the single phase, wherein pH of the single phase composition is between 6.0 and 8.0; and at least 64% water based on a total weight of the single phase composition;

wherein the oxidative compound is sodium chlorite; and wherein the single phase composition exhibits less than 35% loss of the oxidative compound for a period of 24 months at about 25° C.

11. The single phase composition of claim 10, comprising 2.5% of the sodium myristoyl sarcosinate, based on a total weight of the single phase composition, and 0.14% of the oxidative compound, based on a total weight of the single phase composition.

12. The single phase composition of claim 10, wherein the single phase composition is formulated into a form of, at least one of, a mouth rinse, a gum, a gel, a paste, a cream, spray, and a lozenge.

13. The single phase composition of claim 8, wherein the single phase composition is formulated into a form of, at least one of, a mouth rinse, a gum, a gel, a paste, a cream, spray, and a lozenge.

14. The single phase composition of claim 8, further comprising an orally acceptable aqueous vehicle comprising at least one of a humectant, an abrasive, a pharmaceutically acceptable carrier, a fluoride ion source, and a thickening agent.

15. The single phase composition of claim 10, further comprising an orally acceptable aqueous vehicle comprising at least one of a humectant, an abrasive, a pharmaceutically acceptable carrier, a fluoride ion source, and a thickening agent.

16. The single phase composition of claim 1, wherein the single phase composition exhibits enhanced bioavailability within 30 seconds to 120 seconds and wherein the single phase composition exhibits enhanced plaque and biofilm removal, biofilm penetration and disruption, and decreased biofilm regrowth for 24 hours.

17. The single phase composition of claim 1, wherein the single phase composition provides enhanced remineralization and decreased demineralization of teeth.

18. The single phase composition of claim 8, wherein the single phase composition exhibits enhanced bioavailability within 30 seconds to 120 seconds and wherein the single phase composition exhibits enhanced plaque and biofilm removal, biofilm penetration and disruption, and decreased biofilm regrowth for 24 hours.

19. The single phase composition of claim 8, wherein the single phase composition provides enhanced remineralization and decreased demineralization of teeth.

* * * * *